(12) United States Patent
    Steigerwald

(10) Patent No.: US 10,072,274 B2
(45) Date of Patent: Sep. 11, 2018

(54) VECTOR COMPRISING MULTIPLE HOMOLOGOUS NUCLEOTIDE SEQUENCES

(71) Applicant: BAVARIAN NORDIC A/S, Kvistgaard (DK)

(72) Inventor: Robin Steigerwald, Munich (DE)

(73) Assignee: BAVARIAN NORDIC A/S, Kvistgaard (DK)

( * ) Notice: Subject to any disclaimer, the term of this patent is extended or adjusted under 35 U.S.C. 154(b) by 0 days.

(21) Appl. No.: 15/399,588

(22) Filed: Jan. 5, 2017

(65) Prior Publication Data

US 2017/0211098 A1    Jul. 27, 2017

Related U.S. Application Data

(63) Continuation of application No. 14/641,669, filed on Mar. 9, 2015, now Pat. No. 9,540,660, which is a continuation of application No. 13/123,605, filed as application No. PCT/EP2009/008275 on Nov. 20, 2009, now Pat. No. 8,999,637.

(60) Provisional application No. 61/116,672, filed on Nov. 21, 2008.

(51) Int. Cl.
    *C12N 15/86*     (2006.01)
    *C12N 15/863*    (2006.01)

(52) U.S. Cl.
    CPC ...... *C12N 15/8636* (2013.01); *C12N 2799/02* (2013.01); *C12N 2800/22* (2013.01)

(58) Field of Classification Search
    None
    See application file for complete search history.

*Primary Examiner* — Addison D Ault

(57) ABSTRACT

The invention relates to vectors comprising two or more homologous nucleotide sequences and methods for generating them. The invention concerns substituting bases in the homologous nucleotide sequences with different bases that do not alter the encoded amino acid sequence. The invention allows for the reduction of intramolecular recombination between homologous nucleotide sequences, in particular in mammalian cells. The invention further relates to nucleotide sequences containing substituted bases.

3 Claims, 32 Drawing Sheets

Specification includes a Sequence Listing.

```
                    Start F and F_trunc                                          50
F          (1)   ATGGATTTGCCAATCCTCAAAACAAATGCAATTACCACAATCTTTGCTGC
F_trunc    (1)   ATGGATCTCCCCATTCTCAAGACCAACGCCATCACCACCATCTTCGCCGC 51                                                             100
F         (51)   AGTCACACTCTGTTTCGCTTCCAGTCAAAACATCACTGTAGAATTTTATC
F_trunc   (51)   CGTGACCCTGTGTTTCGCCAGCAGCCAGAACATCACCGTGGAGTTCTACC 101                                                            150
F        (101)   AATCAACATGCAGTGCAGTTAGCAAAGGCTATCTTAGTGCTTTAACAACT
F_trunc  (101)   AGAGCACCTGCAGCGCCGTGAGCAAGGGCTACCTGAGCGCCCTGACGACC 151                                                            200
F        (151)   GGTTGGTATACTAGTGTTATAACTATAGAATTAAGTAATATCAAGGAAAA
F_trunc  (151)   GGCTGGTACACCAGCGTGATCACCATCGAGCTGTCCAACATCAAAGAAAA 201                                                            250
F        (201)   TAAGTGTAATGGAACAGACGCTAAGGTAAAATTGATAAAACAAGAATTAC
F_trunc  (201)   CAAGTGCAACGGCACCGACGCCAAAGTGAAGCTGATCAAGCAGGAACTGC 251                                                            300
F        (251)   ATAAATATAAAAATGCTGTAACAGAATTGCAGTTGCTCATGCAAAGCACA
F_trunc  (251)   ACAAGTACAAGAACGCCGTGACCGAGCTGCAGCTGCTGATGCAGAGCACC 301                                                            350
F        (301)   CCAGCAGCCAACAATCGGGCCAGAAGAGAACTACCAAGGTTTATGAATTA
F_trunc  (301)   CCTGCCGCCAACAACAGAGCCAGGCGCGAGCTGCCCCGGTTCATGAACTA F        (351)   TACACTCAACAATACCAAAAATAACAATGTAACATTAAGCAAGAAAAGGA
F_trunc  (351)   CACCCTGAACAACACCAAGAACAACAACGTGACCCTGAGCAAGAAGCGGA 401                                                            450
F        (401)   AAGAAGATTTCTTGGCTTCTTGTTAGGTGTTGGATCTGCAATCGCCAGT
F_trunc  (401)   AGCGGCGGTTCCTGGCTTTCTGCTGGGCGTGGGCAGCGCCATTGCCAGC primer A1
                 451            ------------------->                            500
F        (451)   GGCATTGCTGTATCTAAAGTCCTGCACCTAGAAGGGGAAGTGAACAAAAT
F_trunc  (451)   GGCATTGCCGTGTCTAAGGTCCTGCATCTGGAAGGCGAGGTCAACAAGAT 501                                                            550
F        (501)   CAAAAGTGCTTTACTATCCACAAACAAGGCTGTAGTCAGCTTATCAAATG
F_trunc  (501)   TAAGAGCGCCCTGCTGTCCACCAACAAGGCCGTGGTGTCCCTGAGCAACG 551                                                            600
F        (551)   GAGTTAGTGTCTTAACCAGCAAAGTGTTAGACCTCAAAAACTATATAGAT
F_trunc  (551)   GCGTGAGCGTGCTGACCAGCAAGGTGCTGGATCTGAAGAACTACATCGAC 601                                                            650
F        (601)   AAACAATTGTTACCCATTGTGAACAAGCAAAGCTGCAGCATATCAAACAT
F_trunc  (601)   AAGCAGCTGCTGCCCATCGTGAATAAGCAGTCCTGCAGCATCAGCAACAT
```

Figure 1

```
                651                                                    700
F       (651) TGAAACTGTGATAGAATTCCAACAAAAGAGCAACAGACTACTAGAGATTA
Ftrunc  (651) CGAGACAGTGATCGAGTTCCAGCAGAAGAGCAACCGGCTGCTGGAAATCA 701                                                    750
F       (701) CCAGGGAATTTAGTGTTAATGCAGGTGTAACTACACCTGTAAGCACTTAT
Ftrunc  (701) CCCGGGAGTTCAGCGTGAATGCCGGCGTGACCACCCCCGTGTCCACCTAC 751                                                    800
F       (751) ATGTTAACAAATAGTGAATTATTATCATTAATCAATGATATGCCTATAAC
Ftrunc  (751) ATGCTGACCAACAGCGAGCTGCTGTCCCTGATCAATGACATGCCCATCAC 801                                                    850
F       (801) AAATGATCAGAAAAAGTTAATGTCCAACAATGTTCAAATAGTTAGACAGC
Ftrunc  (801) CAACGACCAAAAGAAACTGATGAGCAACAACGTGCAGATCGTGCGGCAGC 851                                                    900
F       (851) AAAGTTACTCTATCATGTCCATAATAAAGGAGGAAGTCTTAGCATATGTA
Ftrunc  (851) AGAGCTACAGCATCATGAGCATCATCAAAGAAGGTGCTGGCCTACGTG 901                                                    950
F       (901) GTACAATTACCACTATATGGTGTAATAGATACACCTTGTTGGAAACTACA
Ftrunc  (901) GTGCAGCTGCCCCTGTACGGCGTGATCGACACCCCCTGCTGGAAGCTGCA 951                                                   1000
F       (951) CACATCCCCTCTATGCACAACCAACACAAAGGAAGGGTCCAACATCTGTT
Ftrunc  (951) CACCAGCCCCCTGTGCACCACCAACACCAAAGAGGGCAGCAACATCTGCC 1001                                                   1050
F      (1001) TAACAAGAACCGACAGAGGATGGTACTGTGACAATGCAGGATCAGTGTCT
Ftrunc (1001) TGACCCGGACCGATAGGGCTGGTACTGCGACAACGCCGGCAGCGTGTCC 1051                                                   1100
F      (1051) TTCTTCCCAACAAGCTGAAACATGCAAAGTTCAATCGAATCGAGTATTTG
Ftrunc (1051) TTCTTTCCCCAAGCCGAGACTTGCAAGGTGCAGAGCAACAGGGTGTTCTG
                                   <--------------------
                                       Primer B2
               1101                                                   1150
F      (1101) TGACACAATGAACAGTTTAACATTACCAAGTGAAGTAAATCTCTGCAACA
Ftrunc (1101) CGACACCATGAACAGCCTGACCCTGCCCAGCGAAGTGAACCTGTGCAACA 1151                                                   1200
F      (1151) TTGACATATTCAACCCTAAATATGATTGCAAAATTATGACTTCAAAAACA
Ftrunc (1151) TCGACATCTTTAACCCCAAGTACGACTGCAAGATCATGACCTCCAAGACC 1201                                                   1250
F      (1201) GATGTAAGCAGCTCCGTTATCACATCTCTAGGAGCCATTGTGTCATGCTA
Ftrunc (1201) GACGTGTCCAGCTCCGTGATTACCAGCCTGGGCGCCATCGTGTCCTGCTA 1251                                                   1300
F      (1251) TGGCAAAACTAAATGTACAGCATCCAATAAAAATCGTGGAATCATAAAGA
Ftrunc (1251) CGGCAAGACCAAGTGCACCGCCAGCAACAAGAACCGGGCATCATCAAGA
```

Figure 1 (continued)

```
              1301                                               1350
F      (1301) CATTTTCTAACGGGTGTGATTATGTATCAAACAAGGGGGTGGACACTGTA
Ftrunc (1301) CCTTCAGCAACGGCTGCGACTACGTGTCCAATAAGGGCGTGGACACCGTG 1351                                               1400
F      (1351) TCTGTAGGTAATACGTTATATTATGTAAATAAGCAAGAAGGAAAAAGTCT
Ftrunc (1351) TCCGTGGGCAACACACTGTACTACGTGAACAAGCAGGAAGGCAAGAGCCT 1401                                               1450
F      (1401) CTATGTAAAAGGTGAACCAATAATAAATTTCTATGACCCATTAGTGTTCC
Ftrunc (1401) GTACGTGAAGGGCGAGCCCATCATCAACTTCTACGACCCCCTGGTGTTCC 1451                                               1500
F      (1451) CTTCTGATGAATTTGATGCATCAATATCTCAAGTCAATGAGAAGATTAAC
Ftrunc (1451) CCAGCGACGAGTTCGACGCCAGCATCAGCCAAGTGAACGAGAAGATCAAT 1501                                               1550
F      (1501) CAGAGCCTAGCATTTATTCGTAAATCCGATGAATTATTACATAATGTAAA
Ftrunc (1501) CAGTCCCTGGCCTTCATCAGGAAGAGCGACGAGCTGCTGCACAATGTGAA 1551                                               1600
F      (1551) TGTTGGTAAATCCACCACAAATATCATGATAACTACTATAATTATAGTGA
Ftrunc (1551) CGTGGGCAAGTCCACCACCAACTGA-------------------------
                                       stop Ftrunc
              1601                                               1650
F      (1601) TTATAGTAATATTGTTATTATTAATTGCAGTTGGGCTGTTCCTATACTGC
Ftrunc (1576) --------------------------------------------------

1651                                               1700
F      (1651) AAGGCCAGAAGCACACCAGTCACACTAAGCAAGGATCAACTGAGTGGTAT
Ftrunc (1576) --------------------------------------------------

1701           1725
F      (1701) AAATAATATTGCATTTAGTAACTGA    stop F
Ftrunc (1576) -------------------------
```

Figure 1 (continued)

BN_F-trunc optimized vs.BN_F full length
Score = 992 bits (2564), Expect = 0.0, Identities = 524/524 (100%),
Positives = 524/524 (100%), Gaps = 0/524 (0%)

```
F        1    MDLPILKTNAITTIFAAVTLCFASSQNITVEFYQSTCSAVSKGYLSALRTGWYTSVITIE    60
F_trunc  1    MDLPILKTNAITTIFAAVTLCFASSQNITVEFYQSTCSAVSKGYLSALRTGWYTSVITIE    60

F        61   LSNIKENKCNGTDAKVKLIKQELDKYKNAVTELQLLMQSTPAANNRARRELPRFMNYTLN   120
F_trunc  61   LSNIKENKCNGTDAKVKLIKQELDKYKNAVTELQLLMQSTPAANNRARRELPRFMNYTLN   120

F        121  NTKNNNVTLSKKRKRRFLGFLLGVGSAIASGIAVSKVLHLEGEVNKIKSALLSTNKAVVS   180
F_trunc  121  NTKNNNVTLSKKRKRRFLGFLLGVGSAIASGIAVSKVLHLEGEVNKIKSALLSTNKAVVS   180

F        181  LSNGVSVLTSKVLDLKNYIDKQLLPIVNKQSCSISNIETVIEFQQKSNRLLEITREFSVN   240
F_trunc  181  LSNGVSVLTSKVLDLKNYIDKQLLPIVNKQSCSISNIETVIEFQQKSNRLLEITREFSVN   240

F        241  AGVTTPVSTYMLTNSELLSLINDMPITNDQKKLMSNNVQIVRQQSYSIMSIIKEEVLAYV   300
F_trunc  241  AGVTTPVSTYMLTNSELLSLINDMPITNDQKKLMSNNVQIVRQQSYSIMSIIKEEVLAYV   300

F        301  VQLPLYGVIDTPCWKLHTSPLCTTNTKEGSNICLTRTDRGWYCDNAGSVSFFPQAETCKV   360
F_trunc  301  VQLPLYGVIDTPCWKLHTSPLCTTNTKEGSNICLTRTDRGWYCDNAGSVSFFPQAETCKV   360

F        361  QSNRVFCDTMNSLTLPSEVNLCNIDIFNPKYDCKIMTSKTDVSSSVITSLGAIVSCYGKT   420
F_trunc  361  QSNRVFCDTMNSLTLPSEVNLCNIDIFNPKYDCKIMTSKTDVSSSVITSLGAIVSCYGKT   420

F        421  KCTASNKNRGIIKTFSNGCDYVSNKGVDTVSVGNTLYYVNKQEGKSLYVKGEPIINFYDP   480
F_trunc  421  KCTASNKNRGIIKTFSNGCDYVSNKGVDTVSVGNTLYYVNKQEGKSLYVKGEPIINFYDP   480

F        481  LVFPSDEFDASISQVNEKINQSLAFIRKSDELLHNVNVGKSTTNIMITTIIIVIIVILLL   540
F_trunc  481  LVFPSDEFDASISQVNEKINQSLAFIRKSDELLHNVNVGKSTTN----              524

F        541  LIAVGLFLYCKARSTPVTLSKDQLSGINNIAFSN    574
F_trunc  541  ---------------------------------
```

```
                1                                                 50
EBOV-B    (1)   XVTSGILQLPRER RKTSFFVWVIIPFHKVFPIPLGVVFNNTIQVSDIXK
EBOV-S    (1)   XGGLSLLQLPRDKERKSSFFVWVIILQKAFSMPLGVVTKSTLEVTEIQQ
EBOV-Z    (1)   XGVTGILQLPRDRKPTSFFLWVIILFQRTFSIPLGVIHNSTLQVSDVDK
                51                                                100
EBOV-B    (51)  LVCRKISSTSQLKSVGLNLEGNVATMVTATKRWGFRAGVPPKVVNYE
EBOV-S    (51)  LVCKDHLASTDQLKSVGLNLEGSGVSTDIPSATKRWGFRSGVPPKVVSYE
EBOV-Z    (51)  LVCRKISSTNQLRSVGLNLEGNGVATMVSATKRWGFRSGVPPKVVNYE
                101                                               150
EBOV-B    (101) AGEWAENCYNLDIIKEADGSECLPEAPEGMRGFPRCRYVHKVSGTGPCPEG
EBOV-S    (101) AGEWAENCYNLEIKKPDGSECLPPPPDVVRGFPRCRYVHKAQGTGPCPGD
EBOV-Z    (101) AGEWAENCYNLEIKKPDGSECLPAADGIRGFPRCRYVHKVSGTGPCAGD
                151                                               200
EBOV-B    (151) YAFHKEGAFFLYDRLASTIIYRSTTFSEGVVAFLILPETKDFQSPILH
EBOV-S    (151) YAFHKDGAFFLYDRLASSVIYSGVNEAGGVIAFLILAKPKETFLQSPIR
EBOV-Z    (151) FAEHKEGAFFLYDRLASTVIYRGTTFAEGVVAFLILPQAKDFSSHELR
                201                                               250
EBOV-B    (201) PPANMTTDPSSYHTVTLNYVADNFGTNMTNFLFQVDHLTYVQLEPRFT
EBOV-S    (201) PAVNYTENTSSYYATSYLEYEIENPGAQHSTTLFKIINNTFVRLDRPHTP
EBOV-Z    (201) PPVNATEDPSSGYYSTTIRYQATGFGTNETEYLFEVDNLTYVQLESRFT
                251                                               300
EBOV-B    (251) QPIVQLNETIYTNGRRSNTTGTLIWKVNPTVDTGVGEWAFWENKKNFTKT
EBOV-S    (251) QPFQLNDTIHLHQQLSNTTGRLIWTLDANINADIGEWAFWENKNLSEQ
EBOV-Z    (251) QFLQLNETIYTSGKRSNTTGKLIWKVNPEIDTTIGEWAFWETKKNLTRK
                301                                               350
EBOV-B    (301) LSSEELSVIFVPRAQDPGSNQKTKVTPTSFANNQTSKNHEDLVPEDPASV
EBOV-S    (301) LRGEELSFEALSLNETEDDDAASSRITKGRISDRATRKYSDLVPKNSPGM
EBOV-Z    (301) IRSEELSFTVVSNGAKNISGQSPARTSSDPGTNTTTEDHKIMASENSSAM
                351                                               400
EBOV-B    (351) VQVRDLQRENTVPTPPPDTVPTTLIPDTMEEQTTSHYEPPNISRNHQERN
EBOV-S    (351) VPLHIPEGETTLPSQNSTEGRRVGVNTQETITETAATIIGTNGNHMQIST
EBOV-Z    (351) VQVHSQGREAAVSHLTTLATISTSPQSLTTKPGPDNSTHNTPVYKLDISE
                401                                               450
EBOV-B    (401) NTAHPETLANNPPDNTTPSTPPQDGERTSSHTTPSPRPVPTSTIHPTTRE
EBOV-S    (401) IGIRPSSSQIPSSSPTTAPSPEAQTPTTHTSGPSVMATEEPTTPPGSSPG
EBOV-Z    (401) ATQVEQHHRRTDNDSTASDTPSATTAAGPPKAENTNTSKSTDFLDPATTT
                451                                               500
EBOV-B    (451) THIPTTMTTSHDTDSNRPNPIDISETEPGPLTNTTRGAANLLTGSRTT
EBOV-S    (451) PTTEAPTLTTPENITTAVKTVLPQETSNGLITSTVTCILGSLGLRKKST
EBOV-Z    (451) SPQNHSETAGNNNTHHQDTGEESASSGKLGLITNIAGVAGLITGGRRT
                501                                               550
EBOV-B    (501) REITLRTQAKCNPNLHYWTTQDEGAAIGLAWIPYFGPAAEGIYTEGIMHN
EBOV-S    (501) RQTNTKATGKCNPNLHYWTAQEQHNAAGIANIPYFGPGAEGITTGIMHN
EBOV-Z    (501) REAIVNAQPKCNPNLHYWTTQDEGAAIGLAWIPYFGPAAEGIYIEGIMHN
                551                                               600
EBOV-B    (551) QNGLICGLRQLANETTQALQLFLRATTELRTFSILNRKAIDFLLQRWGGT
EBOV-S    (551) QNALVCGLRQLANETTQALQLFLEATTELRTYTILNRKAIDFLLRRWGGT
EBOV-Z    (551) QDGLICGLRQLANETTQALQLFLRATTELRTFSILNRKAIDFLLQRWGGT
                601                                               650
EBOV-B    (601) CHILGPDCCIEPHDWTKNITDKIDQIIHDFIKPFEDQTDNDNWWTGWRQ
EBOV-S    (601) CRILGPDCCIEPHDWTKNITDKINQIIHDFIDNPLENQDNDNWWTGWRQ
EBOV-Z    (601) CHILGPDCCIEPHDWTKNITDKIDQIIHDFVDKTLPDQGDNDNWWTGWRQ
                651                   676
EBOV-B    (651) WVPAGIGITGVILAVIAIKFLL
EBOV-S    (651) WIPAGIGITGIIAIIAIKVCKLLC
EBOV-Z    (651) WIPAGIGVTGVIIAVIALFCICKFVF
```

|  |  | 1 | 50 |
|---|---|---|---|
| EBOV-B non-opt | (1) | ATGGTTACATCAGGAATTCTACAATTGCCCCGTGAACGCTTCAGAAAAAC | |
| EBOV-S non-opt | (1) | ATGGGGGTCTTAGCCTACTCCAATTGCCCAGGAACAAATTTCGGAAAAG | |
|  |  | 51 | 100 |
| EBOV-B non-opt | (51) | ACCATTTTTTGTTTGGGTAATAATCTATTCACAAAGTTTTCCCTATCC | |
| EBOV-S non-opt | (51) | CTCTTTCTTGTTTGGGTCATCATTTATTCCAAAAGGCCTTTTCCATGC | |
|  |  | 101 | 150 |
| EBOV-B non-opt | (101) | CATTGGGCGTAGTTCACAACAACACTCTCCAGGTAAGTGATATAGATAAA | |
| EBOV-S non-opt | (101) | CTTTGGGTCTTGTGACTAACAGCACTTTAGAAGTAACAGAGATTGACCAG | |
|  |  | 151 | 200 |
| EBOV-B non-opt | (151) | TTGGTGTGCCGGCATAAACTTGCCGCCACAAGTCAGCTGAAATCGGTCGG | |
| EBOV-S non-opt | (151) | CTAGTCTGCAAGGATCATCTTGCATCTACTGACCAGCTGAAATCAGTGG | |
|  |  | 201 | 250 |
| EBOV-B non-opt | (201) | GCTTAATCTAGAAGGTAATGGAGTTGCCACAGATGTACCAACAGCAACGA | |
| EBOV-S non-opt | (201) | TCTCAACCTCGAGGGAGCGGAGTATCTACTGATATCCCATCTGCAACAA | |
|  |  | 251 | 300 |
| EBOV-B non-opt | (251) | AGAGATGGGGATTCCGAGCTGGTGTTCCACCCAAAGTGGTGAACTACGAA | |
| EBOV-S non-opt | (251) | AGCGTTCGCGCTTCAGATCTGCTGTTCCTCCAAGGTGCTCAGCTATGAA | |
|  |  | 301 | 350 |
| EBOV-B non-opt | (301) | GCTGGGGAGTGGGCTGAAAACTGCTACAACCTGGACATCAAGAAGGCAGA | |
| EBOV-S non-opt | (301) | CCGGAAGAATGGGCCAAATTCCTACAATCTGTGAATTAAAAGAAGCCGGA | |
|  |  | 351 | 400 |
| EBOV-B non-opt | (351) | TGGTAGCCAATGCCTACTGAAGCCCCTGAGGGGTCTAACAGGCTTCCCTC | |
| EBOV-S non-opt | (351) | CGGGAGCGAATGCTTACCCCACCGGCAGATGGTGCAGAGGGCTTTCCAA | |
|  |  | 401 | 450 |
| EBOV-B non-opt | (401) | GCTGTCCTTTATGTGCACAAGGTTTCTGGAACAGGGCCGTCCCTGAAGT | |
| EBOV-S non-opt | (401) | GGTGCCCCTATGTTCACAAAGCCCAAGGAACCGGGCCCTGCCCAGGTGAC | |
|  |  | 451 | 500 |
| EBOV-B non-opt | (451) | TACGCTTTCCACAAAGAAGGCGCTTCTTCCTGATGATCGACTGGCATT | |
| EBOV-S non-opt | (451) | TACGCCTTTCACAAGGATGGAGCCTTCTTCCTCTACGACAGGCTGGCTTC | |
|  |  | 501 | 550 |
| EBOV-B non-opt | (501) | AACAATCATCTATCGAAGCACCACGTTTCAGAAGGTGTTGTGGCTTTCT | |
| EBOV-S non-opt | (501) | AACTGTAATTTACAGAGGAGTCAATTTTGCTGAGGGGTAATTGCATTCT | |
|  |  | 551 | 600 |
| EBOV-B non-opt | (551) | TGATCCTCCCCGAAAGTAAAAGGACTTTTCCAATCGCCACCACTACAT | |
| EBOV-S non-opt | (551) | TGATATTGGCTAAACCAAAAGAAACGTTCCTTCAGTCACCCCCATTCGA | |
|  |  | 601 | 650 |
| EBOV-B non-opt | (601) | GAACCGGCCCAATATGACAACAGACCCATTCAGCTACTACCAACAGTCAC | |
| EBOV-S non-opt | (601) | CAGGCACTAAACTACACTGAAAATACATCAAGTTATTATGCCACATCCTA | |
|  |  | 651 | 700 |
| EBOV-B non-opt | (651) | ACTTAATTATCTGGCTGACAATTTTGGACCAATATGACTAACTTTCGT | |
| EBOV-S non-opt | (651) | CTTGGAGTATCAAAATCGAAAATTTGGTGCTCAACACTCCACGACCCTTT | |
|  |  | 701 | 750 |
| EBOV-B non-opt | (701) | TTCAAGTGCATCATCTAACTTATGTGCAACTTGAACCAAGATTCACACCA | |
| EBOV-S non-opt | (701) | TCAAAATTGACAATAATACTTTGTTCGTCTGGACAGGCCCCACAGGCCT | |
|  |  | 751 | 800 |
| EBOV-B non-opt | (751) | CAATTCTTGTCCAACTCAATGAGCATTTATACTAATGGGCGTCGCA | |
| EBOV-S non-opt | (751) | CAGTCCCTTTCCAGCTGAATGATACCATTCACCTTCACCAACAGTTGAG | |
|  |  | 801 | 850 |
| EBOV-B non-opt | (801) | CAACACCACAGGAACACTAATTTGGAAAGTAAATCCTACTGTTGACACCG | |
| EBOV-S non-opt | (801) | TAATACAACTGGGAGACTAATTTGGACACTAGATGCTAAATCAATGCTG | |
|  |  | 851 | 900 |
| EBOV-B non-opt | (851) | GCGTAGGTGAATCGGCCTTCTGGAAAATAAGAAGCTTCACAAAAACC | |
| EBOV-S non-opt | (851) | ATATTGGTGAATGGCTTTTTGGAAAATAAAAAATCTCTCCGAACAA | |
|  |  | 901 | 950 |
| EBOV-B non-opt | (901) | GTTCAAGTGAAGAGCCTGTGCGTCATATTTGTACCAAGAGCCCAGGATCC | |
| EBOV-S non-opt | (901) | CTACGTGGAAAGCACCCTGTTCGAAGCTTATCGCTCAACGAGACAGA | |
|  |  | 951 | 1000 |
| EBOV-B non-opt | (951) | AGGCAGCAACCACAAGACCGAAGGTCACTCCCACCAGCTTCGCCAACAAC | |
| EBOV-S non-opt | (951) | AGAAGATGATGCGGCATCGTCCAGAATTACAAAGGGAAGAATCTCCGAC | |

Figure 9A

|                    |        | 1001                                               | 1050 |
|--------------------|--------|----------------------------------------------------|------|
| EBOV-B non-opt     | (1001) | AAAXCTXXAAGAACCACGAAGAXTXGXTTXCAGAGGAXCCXGCXTCAGXX |      |
| EBOV-S non-opt     | (1001) | GGGXCAXXAGXAAGTXTTCGXACCXXXXTTXCAAXGAAXTXCCXXGGGAXX |     |

(Figure 9A, continued — nucleotide alignment of EBOV-B non-opt and EBOV-S non-opt sequences from position 1001 to 2000.)

Figure 9A (continued)

```
                         2001                    2031
EBOV-B non-opt  (2001)   A?TG?TG??TA???T?C?A?AT?T??ACT??A?
EBOV-S non-opt  (2001)   T??T??T??CG???TGCA?GC?G??TTG??G?

1                                                  50
EBOV-B non-opt     (1)   A??G?TTACAT?A?G?AA?TC?A?A?TG??C??GTGA?CG??TCGA?AAA?C
EBOV-Z non-opt     (1)   A??GGCGTTA?A?GAA?AT?GCAG??AC?T?GT?AT?GA?TCAAG?GGA?
                         51                                                 100
EBOV-B non-opt    (51)   A?CA?T?T??G??T?GG?TAA?A?TC?A??TT?CA?A?GTT??CC?TA?C?
EBOV-Z non-opt    (51)   A?CA?C?T??C??T?GG?TAA?A?T?C?A??T??CC?A?G?ACA??TT?CA??
                         101                                                150
EBOV-B non-opt   (101)   ?A??G??C?TAG?T?CA?A?CA?ACA?TC??CCA??TCA?GTGA?A?ACA?A?A
EBOV-Z non-opt   (101)   ?A??T??A??CA?C?A?C?A?TA?GCA?CAT?A?CAG??T?A?GTGA?GT?CA?C?A
                         151                                                200
EBOV-B non-opt   (151)   T?G??G?T?C?GG?ATA?A??TT?C?T??C?A?CA?GT?A?GC?T?GA?ATC?G?T?C??
EBOV-Z non-opt   (151)   C?A??T?TT?T??GT?GACA?A?C?GT?CA?CCA?CA?A?T?A?ATT?GA?GAT?CA??T?GG
                         201                                                250
EBOV-B non-opt   (201)   G??T?AA?T?C?A?GAA?G?TA?A?TGGA??T?T?C??CA?G?ATG?T?A??C?A?CA?G?CA?A??G?A
EBOV-Z non-opt   (201)   A??G?A?A?A?T?C?CAA??A?G??GA?A?T?C??AG?T?G?GC?CA?A?T?GA?C??G?G?CA?T?G?T?CA?A??C?T?A
                         251                                                300
EBOV-B non-opt   (251)   ?A?GA?A?ATG?G?GA?T?CC?A?GCT?CG?T?G?T?T?CA?CC?CA?AAG?T?GT?GA?AC?TA?CG?A
EBOV-Z non-opt   (251)   ?A?A??GA?A?ATG?G?GC??T?CA?A?GT?CC?G?T?G?T?CC?ACC?AAAG?G?TGT?CA?AT?TA?TGA?A
                         301                                                350
EBOV-B non-opt   (301)   G??TG?G?G?A?G?T?GGG?C?TGA?A?AA?C?TG?C?TA?CA?AC?C?T?GGA?CAT?CAA?GA?AA?GC?AGA
EBOV-Z non-opt   (301)   G??TG?G?TGA?A?GG?GG?C?TGA?A?AA?A?TG?C?CTA?CA?A?TC?T?T?GA?AATC?AA?A?A?AAC?CTG?A
                         351                                                400
EBOV-B non-opt   (351)   T?G?TA?G?C?AA?TG?C?TA?C?C?TGA?AG?CC?T?T?GA?GG?G?T?GT?AA?GA?GG?T?C?T?TC?C?T?G
EBOV-Z non-opt   (351)   C?GG?A?GT?A?G?TT?CT?CA?G?C?CA?TG?GC?A?GA?CG?GA?T?CG?GG?T?TT?CC?CC?C
                         401                                                450
EBOV-B non-opt   (401)   ?C?TG?GC?GT?TA?T?CT?GC?A?CAA?GG?T?T?C?T?GA?A?CA?GG?G?CC?GT?CCC?TGA?A?GGT
EBOV-Z non-opt   (401)   ?GT?GC?C?GG?TA?T?CT?GC?AC?A?AAG?T?T?A?T?CA?G?GA?ACG?G?CA?C?CCT?GT?GC?CG?GA?AC
                         451                                                500
EBOV-B non-opt   (451)   ?AC?G?T?T?C?C?A?C?AA?A?GA?A?GG?C?G?G?T?T?C?T?T?CC?TGA?TGAT?CG?AC?T?GG?CA?T?
EBOV-Z non-opt   (451)   ?TT??GC?C?T?T?C?C?A?TA?A?AGA?GG?T?G?C?T?T?C?T?T?CC?C?TGT?A?TGAT?CG?AC?T?T?G?CT?T?C
                         501                                                550
EBOV-B non-opt   (501)   AA?A?AT?CA?T?C?T?AT?GAA?CA?C?CA?CG?T?T?T?CA?G?AAG?G?T?GT?T?GG?C?T?T??CT
EBOV-Z non-opt   (501)   C?A??AG?TTA?T?C?T?A?C?T?GA?G?GAA?T?GA?CT?T?C?CG?CT?GA?AG?G?T?C?T?C?CT?T?CA?T?T?TC
                         551                                                600
EBOV-B non-opt   (551)   ??GA??C?C?T?C??C?G?A?A?A?GT?A?A?A?AA?C?GA?C??TT?T??CCA?A?T?CG?C?CA??AC??ACAT
EBOV-Z non-opt   (551)   ?TGA?TA?CT?G?C?C?CC?A?AG?C?T?A?A?G?A?A?GGA?CT?T?C?T?T?C?AGC?T?CA?C?AC?C??CT??GAGA
                         601                                                650
EBOV-B non-opt   (601)   ?A?A?C??G?G?C?C?AA?AT?GA?C?AACA?G?A?C??CA?T?C?A?G?CTA?C?T?AC?C?A?CA??AGT??A?C
EBOV-Z non-opt   (601)   ?A?GC?C?C?G?G?T?C?AA??GCA?A??GGAG??A?C??C?GT?C?TA?GT?GG??TA?CT?A?T?T?T?AC??A?C
                         651                                                700
EBOV-B non-opt   (651)   ?AC??T??A?A?T??A?T?GT?GG?C?GA?C?A?A??T?T?T?GGA?C?AA?AT?GA?C?T?A?A?C??T?T?C??
EBOV-Z non-opt   (651)   ?A?AT?T?A?GA?T?A?CA??GG?C?T?AC??GG?T?T?T?GA?A?C?CA?A?T?GA?C?AG?A?G??ACT??
                         701                                                750
EBOV-B non-opt   (701)   ?T?C?A?A?T?GGA?TCA?T?C?T?A?A?C?T??AT?G?GC?AA?C?T?T?GA?A?C?C?A?AGA?T?T?A?CA?CC?A
EBOV-Z non-opt   (701)   ?T?CG?A?G?G?T?T?GA?CA?A?T?T?T?GA?C?C?T?A?C?GT?C?C?A?A?C?T?T?GA?AT?C?A?AGA?T?T?CA?CA?CC?A
                         751                                                800
EBOV-B non-opt   (751)   ??A?A?T?T?C?C?T?GT?T?C?CA?A?T?C?A?A?T?GA?GA?C?CA?T?T?A?T?A?C?T??A?T?GG?CGT?CG?C?A?
EBOV-Z non-opt   (751)   ??A?G?T?T?C?T?GC?T?T?CA?G?T?T?GA?A?T?GA?GA?CA?A?T?A?T?A?T?A?CA?A?GT?GG?AAAA?G?A?
                         801                                                850
EBOV-B non-opt   (801)   ?A?A?C?A?C?C?A?C?A?GGA?C?A?C?T?AA?T?T?T?GGA?A?A?GT?A?AA?T?C?C?T?ACT?G?T??T?A?CA??CG
EBOV-Z non-opt   (801)   ?A?A?T?A?C?C?A?C?GG?GA?A?A?A?C?T?AA?T?T?T?GA?A?GT?C?A?AC?C??C?GA?AA?T?G??T?A?C??AA
                         851                                                900
EBOV-B non-opt   (851)   GCG?A?G?T?G?A?A?T?G?G?G?A?C??C??T?T?GGA?A?A?A?T?A?A?G?A?A?G?A?A?C??T?T?CA?CA?A?A?A?A?CC
EBOV-Z non-opt   (851)   CAA??C?G?G?G?C?A?G?T?G?G?G?C??C?C??T?T?CT?GGA?A?A?A?C??T?AA?A?A?A?A?A?A?C??C?T?CA?CT?A?GA?A?A
```

Figure 9A (continued)

```
                         901                                              950
EBOV-B non-opt  (901)  C  TCA  GTGAAGAGC  CTC G CATAT  GT C  AAGA CCCAGG  TCC
EBOV-Z non-opt  (901)  A  CGC  GTGAAGA T  TGTC TT CACAG  TGTATCA AC GAGCCA  AAA
                         951                                             1000
EBOV-B non-opt  (951)  AGG     CAAC  AGAAGA  GAAGGTCA   C CCA  CAG  TTC  CCA  CA  C
EBOV-Z non-opt  (951)  CAT    GTGGT  AGAGTC  GGC  CGAA  CTT CTT  CGA CCAGGGA C AA  A
                        1001                                             1050
EBOV-B non-opt (1001)  A    CT CA GA  CA  GA GA T  GT  C  AGGA  C  G  T  A  
EBOV-Z non-opt (1001)  C    AA T AAG  CCACA  A AT CA  GC TTCAGAA  TT CT CTGC A  
                        1051                                             1100
EBOV-B non-opt (1051)    TCA GT  GAGAC TCCAGA    AA ACA AGTG C  ACC C AC  CC
EBOV-Z non-opt (1051)    TCA GT  CACAGT CAAGGA    GA GCTG  AGT  T  CAT  T A CAA
                        1101                                             1150
EBOV-B non-opt (1101)  AGACA GTCCC  A  A  CTGAT  C CCGA  ACA TGGAGG A CA ACCA
EBOV-Z non-opt (1101)  CCTTG CACAAT T  CA GAGTCC   AATC  CTC CAACCA A C GGTC
                        1151                                             1200
EBOV-B non-opt (1151)   CAG  C  TA GAA CACCA ACATTTCCAGA A C A CA AGAGAGGA  C
EBOV-Z non-opt (1151)   GGA  A  AG CACC ATAAT CACCCGTGTAT A A T GA CATCTCTG G
                        1201                                             1250
EBOV-B non-opt (1201)  AAC  C CGC CACCCCG A AC  CT CGC A ACC AATCC C CCA  ACA ACA C AC
EBOV-Z non-opt (1201)  GCA  A TCA GTT GAAC A  CA   A CG  A GAA CAGA  AAC  ACA G  AC G
                        1251                                             1300
EBOV-B non-opt (1251)   C  GTCG  A  AC  CAAGACGGT  AGCGGAC  AGTT  CC  ACA  ACAC
EBOV-Z non-opt (1251)   T  CGAC  A T  CT  GCCACGACC  CAGCCGG  CCCC  AAA AG C AGAGA
                        1301                                             1350
EBOV-B non-opt (1301)  C T  CC  CGCCCAGTCCCA  CAG ACAA  CCT  C  A CA  ACGA GAG
EBOV-Z non-opt (1301)  A A  AA  ACGAGCAAGAGC A TGA TTCC  GGA  C  G  GCC ACCACA ACA
                        1351                                             1400
EBOV-B non-opt (1351)   C  A  ATTCC  AC  CAAT  A AA  AA  C ATGA  AC  GACAGCAA  T  G
EBOV-Z non-opt (1351)   GT CC CAAAA C A  GCGA  A CCG TGG CA  CA A A ACTCATC A C A
                        1401                                             1450
EBOV-B non-opt (1401)   CCC A  CC  A TTG AC ATCAG  GAGTCTACAGA  C CA GACC  C  CA C  
EBOV-Z non-opt (1401)   GAT  C  GG  A GAA GA GTGCC AGCAGCGGGA    TA  CTT  A TAC A
                        1451                                             1500
EBOV-B non-opt (1451)   CA  CA CAAGA  G  C T C AAT C C GACA GGTCA  GA CA A C C GA
EBOV-Z non-opt (1451)   A CT ATTGCT GGAGTCC CA GGACTGA C ACAGG GGGA  AACAA CT C  
                        1501                                             1550
EBOV-B non-opt (1501)   G  AAATC CCC GAGAACACAAGC AAATC AAC A AAA CC ACAC
EBOV-Z non-opt (1501)   GA AAGCA TTG C ATGCTC AAC C AAATG CA CCC TAATTT ACAT  
                        1551                                             1600
EBOV-B non-opt (1551)  T  GA CA C CA GATGAAC GG C C CATT G TTT AGC C TGGATAC TT
EBOV-Z non-opt (1551)  C  GGA TA CT CAGGATGAAGGT GC TGCAA TC GAC GG C TGGATAC AT
                        1601                                             1650
EBOV-B non-opt (1601)  AC T    CC   AGC AGAGGGAA TT T CG AAG G A AA TGCA A T
EBOV-Z non-opt (1601)  AT T CGG  CC AGCAGCC AGGGAA TTT A CATAGAG G C TAATGCACAA T
                        1651                                             1700
EBOV-B non-opt (1651)   AAA TGGC AA TT GC G GT CAG G AGC A AG CAAA T GA  ACGACT C
EBOV-Z non-opt (1651)   AAGATGGTT A A C  T TG GT TT CAGACAG CT GGCC AACGAC GACTCA
                        1701                                             1750
EBOV-B non-opt (1701)  AG C CA AGT A A T T GCGT CT AC CAC GGAAT GG CACTT  C CTA
EBOV-Z non-opt (1701)  AG CTCTT AAC GT TC CTGAGA CC ACAA CTGAGCTA GCAC CTTT CA A
                        1751                                             1800
EBOV-B non-opt (1751)   AT GA AT GA AAAA GC A CC AAC TTT A GC C AAA GATG GGAGAA  G
EBOV-Z non-opt (1751)   CC CAACC T AAGC CAAT GATTC T GC TG GCAGC ATG GC C GCACA
                        1801                                             1850
EBOV-B non-opt (1801)                CT A  C  AGAT GC T A  T GA G CC ATGATT GAC TAA
EBOV-Z non-opt (1801)                CACATC G GCA CG AC T CT G AT C AA CCACATGA TTGGACC AA
```

Figure 9A (continued)

```
                    1851                                              1900
EBOV-B non-opt (1851) GAACATTATTGACAAATAGATCAAATCATTCATGATTCATTGATAAAC
EBOV-Z non-opt (1851) GAACATAACAGACAAAATTGATCAGATTATTCATGATTTTGTTGATAAAA
                    1901                                              1950
EBOV-B non-opt (1901) GTCTACCAGATCAAACAGATAATGACAATTGGTGGACAGGGTGGAGGCAA
EBOV-Z non-opt (1901) GCCCTTCCGGACCAGGGGGACAATGACAATTGGTGGACAGGATGCAGACAA
                    1951                                              2000
EBOV-B non-opt (1951) TGGGTTCTGCCGGGATCGGGATCACGGGGGTAATAATCGCAGTTATAGC
EBOV-Z non-opt (1951) TGGATACGGCAGGTATTCGAGTTACAGGCGTTATAATTGCAGTTATCGC
                    2001            2031
EBOV-B non-opt (2001) ACTGCTGTGTATTGCAAATTCTACTCTAA
EBOV-Z non-opt (2001) TTTATTCTGTATATGCAAATTTGTCTTTAG 1                                                50
EBOV-S non-opt  (1)  ATGGGGCGTCTTAGCCTACTCCAATTGCCCAGGGACAAATTCGAAAAG
EBOV-Z non-opt  (1)  ATGGGCGTTACAGGAATATTGCAGTTACCTCGTCATCGATCAACAGGAC
                    51                                               100
EBOV-S non-opt (51)  CTCTTCTTGTTGGCTCATCACTTATTCCAAAGGCCTTTCATGC
EBOV-Z non-opt (51)  ATCATTCTTTCTTTGGTAATTACTTTTCCAAGAACATTTCATCC
                    101                                              150
EBOV-S non-opt (101) GTTTGCTGCTGTGACTAACAACAACTTTAGAAGTAACAGAGATTGACCAG
EBOV-Z non-opt (101) CACTTGGAGTCATCCACAATAGCACATTACAGGTTAGTGATGTCGACAAA
                    151                                              200
EBOV-S non-opt (151) CTAGCTCTGCAAGGATCATCGTGCATCTACTGACCAGCTGAAATCAGTGG
EBOV-Z non-opt (151) CTAGCTTGTCGTGACAAACTGTCATCCACAAATCAATTGAGATCAGTGG
                    201                                              250
EBOV-S non-opt (201) TCTCAACCTCGAGCCGAGCCGAAGTATCTACTGATATCCCATCTGCAACAA
EBOV-Z non-opt (201) ACTGAATCTCGAAGGGAATGGACTGGCAACTGACGTGCCATCTGCAACTA
                    251                                              300
EBOV-S non-opt (251) AGCGTTGGGGCTTCAGATCGGTGTTCTGCCAAGTCGTCAGCTATGAA
EBOV-Z non-opt (251) AAAGATGGGGCTTCAGGTCCGGTGTCCACCAAAGGTGGTCAATTATGAA
                    301                                              350
EBOV-S non-opt (301) GCGGGAGAATGGGCTGAAAATTGCTACAATCTTGAAATAAAGAAGCCGCA
EBOV-Z non-opt (301) GCTGGTGAATGGGCTGAAAACTGCTACAATCTTGAAATCAAAAACCTGA
                    351                                              400
EBOV-S non-opt (351) GAAAGCGAATGCTTACCCCACTGCCAGTGTGTCAGAGCTTTCGAA
EBOV-Z non-opt (351) GGGCAGTGAGTCTACCAGCAGCGCCAGACCGGATTCGGGCTTCCGCC
                    401                                              450
EBOV-S non-opt (401) GGTGCCGCTATGTTGACAAAGCCCAAGGAACCGGGCCTTCCCAAGTGAC
EBOV-Z non-opt (401) GGTGCCCGGTATGTGCACAAAGTATCAGGAACGGGACGTGTGCCGACAC
                    451                                              500
EBOV-S non-opt (451) TACGCCCTTTCACAAGGATGGAGCTTTCTTCCCTCTATGACAGGCTGGCTTC
EBOV-Z non-opt (451) TTTGCCTTCCATAAAGGGGTGCTTTCTTCCTGTATGATCGACTTGCTTC
                    501                                              550
EBOV-S non-opt (501) AACTGTAATTTACAGAGCAGTCAATTTGCCTAGCAGGTAATTCCATTCT
EBOV-Z non-opt (501) CACAGTTATCTACCGAGCAACGACTTTCGCTGAGGTGTCGTTGCATTTC
                    551                                              600
EBOV-S non-opt (551) GATATTGCTAAACCAAAAGAAACGTTCCTCAGTCACCCGCATCGA
EBOV-Z non-opt (551) TGATACTGCCCAAGCTAAGAGGACTTCTCAGCTCACACCCTTGACA
                    601                                              650
EBOV-S non-opt (601) GAGCAGTAAACTACACTGAAAATACAACAAGTTATATGCCAGATCCTA
EBOV-Z non-opt (601) GAGCCGGTCAATGCAACGCAGGACCCGTCAGTGGCTACTATTCTACCAC
                    651                                              700
EBOV-S non-opt (651) CTGGAGTATGAAATCGAAAAATTTGTGCTCAACACTCCACGACGCTT
EBOV-Z non-opt (651) AATTAGATATCAGGCTACCGGTTTTGAACCATGAGAAGAGTACTGT
                    701                                              750
EBOV-S non-opt (701) TCAAAATTTACAATAATACTTTTGTTGTCGGACAGGCCCCAGACGCT
EBOV-Z non-opt (701) TCGAGGTTGACAATTTGACCTACCGTCAACTTGAATCAAGATTCACACCA
```

Figure 9A (continued)

```
                         751                                              800
EBOV-S non-opt   (751)   ...
EBOV-Z non-opt   (751)   ...
                         801                                              850
EBOV-S non-opt   (801)   T..TA.AA.TGGA.AC.AA.TT.GACAC.AGATGC.AA.A..CAA.GCTG
EBOV-Z non-opt   (801)   C..AT.CCA.GGGA.AA.AA.TT.GGAAGGTCA.CC.CGAA.TTGA.A.AA
                         851                                              900
EBOV-S non-opt   (851)   AT..T..T..AT..C..T..TT..GGAAA.T.AA.A.A.AATCT.T.CGA.CA.
EBOV-Z non-opt   (851)   CA.AT.C.GG.AG.T.G.CC.TT.C.T.GG.AA.A.CT.AAA.AA.CCT.ACT.AG.A.A.A.
                         901                                              950
EBOV-S non-opt   (901)   C.AC.GTG.A.A.A.GC.TGT.C.TT.C.GA.AGC.TT.TA.C.GCT.AAC.AGA.C.AGA
EBOV-Z non-opt   (901)   A.TT.C.CA.GT.GAA.GA.GT.TG.TC.TT.T.CAC.AGT.TGT.AT.C.AAA.C.GGA.CC.AA.A.A
                         951                                             1000
EBOV-S non-opt   (951)   AGA.CGA.TGA.T.GC.GGCAT.C.GT.C.AG.AA.TT.AC.AAAG.GGAAGA.ATCT.C.G.A.C.C
EBOV-Z non-opt   (951)   CAT.CAG.TC.G.TCA.GAGTCC.CG.C.G.C.GA.AC.TT.C.TTCC.G.ACCC.A.GGGACC.A.A.C.A
                        1001                                             1050
EBOV-S non-opt  (1001)   GGG.C.CA.C.CAGGA.A.GT.A.TT.CGGA.CC.T.C.T.T.C.AA.G.AA.TC.CC.T.GGA.T.C
EBOV-Z non-opt  (1001)   CAA.CA.A.C.TGAAG.A.CC.A.CAAAAT.CA.T.C.GC.T.TC.A.GA.A.A.TT.CC.T.C.T.GCAA.T.C
                        1051                                             1100
EBOV-S non-opt  (1051)   G.T.T.C.A.T.C.CAC.AT.A.C.AG.AAG.C.GG.A.AA.C.AAC.A.T.T.C.C.G.T.C.T.A.GAA.T.T.C
EBOV-Z non-opt  (1051)   G.T.T.CAA.GT.GCAC.G.T.C.AA.GGA.A.GG.A.AG.C.TGC.A.G.T.G.T.C.G.C.A.T.C.T.A.ACAA.C
                        1101                                             1150
EBOV-S non-opt  (1101)   GACA.C.AAGGTCGAAGAGTAG.CT.GTGA.A.CA.C.T.C.AGGAGA.C.C.A.TTA.C.A.C.GAGA
EBOV-Z non-opt  (1101)   CCTT.G.CCACAATCTCCACGAG.T.CCCC.A.AT.C.C.C.T.CACAA.C.C.A.AACC.A.A.G.GTC
                        1151                                             1200
EBOV-S non-opt  (1151)   C.A.C.CTGCA.A.CA.ATTATAGGC.A.C.TAA.C.C.GCA.A.CC.ATA.T.GC.A.GA.TCT.C.CACC
EBOV-Z non-opt  (1151)   C.G.C.ACAAC.A.GC.A.CCCATAAT.A.C.C.C.C.C.GTGT.A.TA.AC.T.TG.AC.A.TC.TC.T.GAG
                        1201                                             1250
EBOV-S non-opt  (1201)   ATCGGGAT.A.AGACCGAGCTCCAG.C.C.AA.ATCC.G.GAGTTC.CTCACCGA.C.CAC
EBOV-Z non-opt  (1201)   GCAACTCA.C.GTTGAACAACATCA.C.C.GC.A.GAA.G.AGACAA.C.GACAGC.A.C.AGC
                        1251                                             1300
EBOV-S non-opt  (1251)   GG.CACCAAGC.C.C.TGAGC.C.TCAGA.CCC.C.CACAACC.C.ACA.C.ATCA.C.GTCCAT
EBOV-Z non-opt  (1251)   CT.C.CGACACT.C.C.CTCT.G.C.CACGA.CCG.C.AGC.C.GGA.C.C.C.C.AAAAG.C.AGAGA
                        1301                                             1350
EBOV-S non-opt  (1301)   CAGTGA.TGG.C.C.A.C.C.GA.C.GAAC.C.AACAACA.C.CACCGGGAAG.C.T.C.C.C.CGGC
EBOV-Z non-opt  (1301)   ACACCA.A.CA.C.GA.G.C.AA.G.AGCA.C.TGACTTC.C.TGGACCCCGC.C.A.C.C.A.ACA
                        1351                                             1400
EBOV-S non-opt  (1351)   CCAA.C.AAC.A.G.A.AGCACC.C.ACTCT.C.A.C.CAC.C.CCAG.A.A.A.T.C.TAACAACAGC
EBOV-Z non-opt  (1351)   AGTC.C.CCA.A.A.C.CACAG.G.GAGAC.C.G.C.TGG.C.AACA.C.A.A.C.A.CTCATCACCA
                        1401                                             1450
EBOV-S non-opt  (1401)   GC.T.T.AAAACT.C.TCCT.C.CCACAGGAGTC.C.ACAA.GCAAC.C.GTCT.AA.TAA.CTT
EBOV-Z non-opt  (1401)   AG.A.T.ACCGGA.C.AAGA.G.AGTGCCAGCAG.C.GGGA.AGCTAG.C.CTT.AA.TT.A.C.CA
                        1451                                             1500
EBOV-S non-opt  (1451)   CA.C.AG.TAAC.A.C.GGA.T.TCTT.C.GGAGTC.T.TGGGCTTC.C.AA.A.AC.C.C.AGCAG.C
EBOV-Z non-opt  (1451)   AT.A.CT.A.T.TGCT.C.C.AG.T.CGCAC.C.ACTGA.T.CACAGGCGG.C.GAA.C.A.AACTC.C
                        1501                                             1550
EBOV-S non-opt  (1501)   .C.C.CAA.A.C.T.AACAC.A.C.AA.A.GC.CACGGGTAAG.T.GC.AA.TC.C.AAC.T.T.AC.A.C.T.A
EBOV-Z non-opt  (1501)   .C.GAA.GC.AA.T.TGTC.AA.T.GC.C.TCAACCCA.AA.T.GC.AAC.C.CTAAT.T.T.AC.A.T.T.A
                        1551                                             1600
EBOV-S non-opt  (1551)   CT.C.GA.CTGC.A.C.AA.GA.AC.AAC.A.T.AA.C.GCTG.C.T.GGA.T.TG.C.C.C.TGGA.TC.C.C.GT
EBOV-Z non-opt  (1551)   CT.C.GA.CTA.C.T.C.AG.G.AT.GAAGG.T.GC.T.G.C.AAT.C.G.GA.C.TGG.C.C.C.TGGA.TA.C.C.AT
                        1601                                             1650
EBOV-S non-opt  (1601)   .AC.TT.C.GA.C.GG.T.GT.C.GG.AA.GG.C.ATA.TA.C.T.C.AAG.C.CTGA.TG.C.ATA.C
EBOV-Z non-opt  (1601)   .AT.T.C.GG.GC.C.AG.CA.C.CC.GAG.G.GAATT.AC.TA.GG.G.GCT.AAT.CAC.AAT
                        1651                                             1700
EBOV-S non-opt  (1651)   .A.AAT.GCC.TTA.G.TC.T.C.T.GG.ACTT.AG.C.AAC.TT.GC.AAA.T.GAA.C.AA.C.C.C.C
EBOV-Z non-opt  (1651)   .A.AG.A.T.GT.T.T.AA.C.TC.T.C.G.GT.T.GA.GACA.G.TG.C.AAC.GAG.A.C.C.A
                        1701                                             1750
EBOV-S non-opt  (1701)   AGCTCT.GC.A.GC.TTT.T.CT.T.A.AGAGCC.CA.AC.GGAGC.TGC.GGA.CA.TA.TA.C.A
EBOV-Z non-opt  (1701)   AG.C.C.T.T.CAA.C.GT.GT.CC.T.GA.GA.GCC.CA.AC.TGAG.C.TAC.GCAC.CT.T.T.CAA
```

Figure 9A (continued)

```
                     1751                                               1800
EBOV-S non-opt (1751) TACTCAATAGGAAGGGCATAGATTTCCTTCTGGGACGATGGGGGGGACA
EBOV-Z non-opt (1751) TCCTCAACCCTAAGGCAATGATTTCTTGCTGCAGCGATGGGGGGCACA
                     1801                                               1850
EBOV-S non-opt (1801) TGGAGGATCCTGGGACCAGATTGTTGCATTGAGCCACATGATTGGACAAA
EBOV-Z non-opt (1801) TGGCACATTCTGGGACCGACTTCTGTATCGAACCACATGATTGGACCAA
                     1851                                               1900
EBOV-S non-opt (1851) AAACATCACTGATAAAATCAACCAAATCATCCATGATTTCATCGACAACC
EBOV-Z non-opt (1851) GAACATAACAGACAAAATTGATCAGATTATTCATGATTTTGTTGATAAAA
                     1901                                               1950
EBOV-S non-opt (1901) CCTTACCTAATCAGGATAATGATGATAATTGCTGGACGGGCTGGAGACAG
EBOV-Z non-opt (1901) CCCTTCGGGACCAGGGGGACAATTACAATTGCTGGACAGGATGGAGACAA
                     1951                                               2000
EBOV-S non-opt (1951) TGGATCCCTGCAGGAATAGGCATTACTGGAATTATTATTGCAATATTTGC
EBOV-Z non-opt (1951) TGGATACCGCACGTATTGGAGTTACAGGCGTTATAATTGCAGTTATCGC
                     2001              2031
EBOV-S non-opt (2001) TCTTCTTTGCGTTTGCAAGCTGCTTTGCTGA
EBOV-Z non-opt (2001) TTTATTCTGTATATGCAAATTTGTCCTTTAG
```

Figure 9A (continued)

```
              1                                                50
EBOV-B opt  (1)  ATGGTCACATCTGGAAATTCCAGCTCCGTAGGGAACGGTTCCGGAAAA
EBOV-S opt  (1)  ATGGCGGCCTGAGCCTGCTGCAGCTGCTCCGGACAACTTCCCAAGTC
              51                                               100
EBOV-B opt  (51) CAGTTTCTTTGTCTGGCTCATCATCCCCTTCCATAAGGTGTTCCCTATCC
EBOV-S opt  (51) CAGCCTTCTTCCGGTGGGTGATCATCCGTTCCAGAAAGCCTTCAGCATGG
              101                                              150
EBOV-B opt  (101) CCCTGGGGGCTCGTCCATAACAATACATTGCAAGTGTCAGATATCCAATAAC
EBOV-S opt  (101) CCCTGGGCGTGCTGACCAACAGCATCCTGAAGTGACCAGATCACCAG
              151                                              200
EBOV-B opt  (151) TTGGTCTGTCGCGATAAAGTGATCTCCTCTCAGCTGAAAAGCGTCGG
EBOV-S opt  (151) CTGGTCGTGCAAGGACCACCTGGCCAGCACCGATCAGCTGAAGTCCGTGGC
              201                                              250
EBOV-B opt  (201) CCCAACCTCGAAGGGAATGGTCGCGAATGATGTCCCTACTGCCACCAA
EBOV-S opt  (201) CCCTGAACCTGGAAGGCAGCGGCCTGAGCAACCATCCCAGCGCCACCA
              251                                              300
EBOV-B opt  (251) AACGATGGCTTTCCGGCTGGTCCCCCAGAAGTTGTCAACTATCAA
EBOV-S opt  (251) AGAGATGGGCCTTCAGATCGACCTGCCCCAAGGTGGTGTCTTATGAG
              301                                              350
EBOV-B opt  (301) GCTGCCGAATCGGCAGAGAATTGCTATAATCTGGACATTAAAAAGGCCGA
EBOV-S opt  (301) GCCCTGGAGTGGGCCAGAACTGCTACAACCTGGAAATCAAGAACCCGA
              351                                              400
EBOV-B opt  (351) TCGGTCCGAGTGTCTCCGTGAAGCTGCTGAGGCTGCTCGGGATTCCGAA
EBOV-S opt  (351) CGGCAGCGAGTGTCTGCCTCCCCCTCCCGATGGCGTGAGAGGCTTCCCCC
              401                                              450
EBOV-B opt  (401) GATGTCCCTACGTCCATAAAGTGTCTGCCACCCGCCCTTGCCCTAAAGA
EBOV-S opt  (401) GGTCCAGATACCGTGCACAAGGCACAAGCCATCCGGTCCATGCCCAGCAAC
              451                                              500
EBOV-B opt  (451) TACCCCTTTCATAAAGAAGGGCCCTTTTCCTCCATGATCGGCCTGGTTT
EBOV-S opt  (451) TACCCCTCCAACAAGGACCGGCCCTTTTCCTGGACCACCGGCTGGCCT
              501                                              550
EBOV-B opt  (501) ACAATATCGATCGCTCTACTACGTTGTCGAGGGCGTGCGTCGTTTTT
EBOV-S opt  (501) CACCGTGATCACCGGGCGTGAACTTGCCGAGGGCGTGATCGGCTTC
              551                                              600
EBOV-B opt  (551) TCATCCTCCCGAGACAAGGAAAGATTTCTGTTCAGAGTCCCGCCCTGAT
EBOV-S opt  (551) TGATCCTGGGCAAGCTGCAAAGAGGACATGCTGCAGAGCCTCCCCATCGG
              601                                              650
EBOV-B opt  (601) AAGCCTGCCAATATGATTACCGATCGTTCGTCTGACTATCATACCGTGAC
EBOV-S opt  (601) GAGGCCTGAACTACAACCGAGACACCAGCAGCACCTACGCCACCTCCTA
              651                                              700
EBOV-B opt  (651) ACTCAATTATGTCGCTGATAACTTGGCACTAACATGACCAACTTTCTCT
EBOV-S opt  (651) CCTGGAATACAGATCGAGAACTTCGAGCCCCAGCACAGCACCACCCTGT
              701                                              750
EBOV-B opt  (701) TCCAGGTCGACCACTGAGAAATGTCGAGTCCGAGCCTGCTTTACCCCA
EBOV-S opt  (701) TCAAGATCGACAACAACACCTCCTGCGGTGGACAGACCCACACCCCC
              751                                              800
EBOV-B opt  (751) CGGTTCCTGGTCCAGCTCAATGAAGTATTGTATACTAACGGACGGGGCC
EBOV-S opt  (751) CAGCTTTCTGTTCCAGCTGGAACGACAACATCCATCTGCATCAGCAGCTGTC
              801                                              850
EBOV-B opt  (801) TAATAGCACCGGGACCCTCATTGGAAAGTCAATCCCACTGTCGATACC
EBOV-S opt  (801) CAACACCACCGGCAGATGATCCTGGACCCTGGACGCCAACATCAACGCCC
              851                                              900
EBOV-B opt  (851) GCGTCCGAGAGTGGCCTTTTGGAAAACAAGAATAACTTTACCAAGACC
EBOV-S opt  (851) ACATCCGTGAATGGCTTTTTGGCGAACAAGAAGAATCTGAGCGAGCAG
              901                                              950
EBOV-B opt  (901) CTGAGTAGCGAGGAACCTGTCTGGGATCTTTGTGCCTCGCGCTCAGGATCC
EBOV-S opt  (901) CTCCGGGGCGAACAGAGCAGCTCGAGGCCCTGAGCCTGAACGAGACAGA
              951                                              1000
EBOV-B opt  (951) TGGATCCAACAGAAAACCAAGTGCACCTACATCTTTTGCCAACAACC
EBOV-S opt  (951) GGACGACGACGCCGCCACCAGCCGCATCAGCAAGGGCCGGATCAGCCGACC
              1001                                             1050
EBOV-B opt  (1001) AGACAAAGCAAGAACCTGAGGACCCGTCCCCGAAGATCCTGCCTCTGCC
EBOV-S opt  (1001) GGGCCACCAGAAAGTACAGCCAGTGCTGCCCCAAGAACAGCCCGGCATC
```

```
              1951                                              2000
EBOV-S opt  (1951)  ....AC.T..C.C...A.C...A.C..T...AT....
EBOV-Z opt  (1951)  ...T.A...GA.T..G.GA...G.GA.T.C..G.A..G
                    2001                2031
EBOV-S opt  (2001)  T..CC.....G.G...A.GC..C..G....
EBOV-Z opt  (2001)  C..GT...GA.C...A.T..G.GT...
```

Figure 9B (continued)

VECTOR COMPRISING MULTIPLE HOMOLOGOUS NUCLEOTIDE SEQUENCES

CROSS REFERENCE TO RELATED APPLICATIONS

This application is a continuation application of U.S. application Ser. No. 14/641,669, filed on Mar. 9, 2015, (now U.S. Pat. No. 9,540,660), which is a continuation of U.S. application Ser. No. 13/123,605, filed on Apr. 11, 2011 (now U.S. Pat. No. 8,999,637), which is a National Phase application under 35 U.S.C. § 371 of International Application No. PCT/EP2013/055483, filed Mar. 15, 2013, and claims the benefit under 35 U.S.C. § 119(e) of U.S. Provisional Patent Application 61/678,367 filed Aug. 1, 2012, the disclosures of which are incorporated by reference herein in their entirety.

BACKGROUND OF THE INVENTION

The phenomenon of homologous recombination of nucleic acids involves physical breaking and crosswise rejoining of nucleic acid strands within homologous sequences. Recombination and gene conversion in mammalian cells have been studied by many groups who have monitored the reconstruction of selectable genes after infection with appropriately constructed viral or plasmid substrates. (Chakrabarti et al., Mol. Cell. Biol. 6:2520-2526, 1986). The results of these experiments indicate that cells efficiently support both intra- and intermolecular recombination and gene conversion. (Id.) Intermolecular recombination refers to recombination between homologous sequences present on two different nucleic acid molecules, while intramolecular recombination refers to recombination between homologous sequences present on a single nucleic acid molecule.

Intermolecular recombination can occur between genes in a plasmid or virus and homologous sequences within a cell. (Miller et al., Mol. Cell. Biol. 6:2895-2902, 1986.) This type of recombination can cause the generation of an infectious virus from an attenuated virus. Fuller et al. codon-optimized the separated sequences of the HIV-1 gag and the HIV-1 pol gene to increase its expression in mammalian cells. These optimizations also reduced identity of nucleotides in an overlapping region of about 200 base pairs present in the gag-pol gene of HIV, which also resulted in reduced levels of intermolecular recombination between the gag and pol open reading frames placed on two independent plasmids and the truncated gag gene contained in a recombinant retroviral vector. (Fuller et al., Hum. Gene Ther. 12:2081-2093, 2001.)

Intramolecular recombination can occur with vectors in which duplicated regions of a gene or a gene fragment are present as direct repeats separated by intervening sequences. This type of recombination generally results in the deletion of the intervening sequences and one copy of the repeated sequences. The frequency of intramolecular recombination is generally a great deal higher than for intermolecular recombination.

The level of intramolecular recombination within a plasmid vector has been quantitated in mammalian cells. (Rubnitz and Subrami, Mol. Cell. Biol. 4:2253-2258, 1984.) Depending upon the size of the homologous regions, the frequency of intramolecular recombination within a transfected plasmid DNA varied between 0.306% and 0.002%. (Id.) Low recombination efficiencies were seen with as little as 14 bases of homology. (Id.)

Intramolecular recombination between homologous sequences has been also documented in a number of animal viruses including picornaviruses, influenza virus, adenovirus, and poxviruses. (Gritz et al., J. Virol. 64:5948-5957, 1990). In vaccinia viruses, it has been shown that tandemly duplicated sequences are genetically unstable. (Id.) In viruses, a level of intramolecular recombination has been seen that is much higher than that seen with plasmid vectors.

For example, in a retrovirus, the frequency of recombination between two identical sequences in the same RNA molecule was found to be about 62%. (Zhang et al., J. Virol. 75:6348-6358, 2001). 99% of these recombinations were intramolecular (between two sequences on one RNA molecule), as opposed to intermolecular (between two RNA molecules). (Id.) With adeno-associated virus, intramolecular recombination was also found to be far more efficient than intermolecular recombination. (Choi et al., J. Virol. 79:6801-6807, 2005). Herpes simplex virus type 1 has also been shown to exhibit high levels of recombination. (Dutch et al., J. Virol. 66:277-285.) In poxviruses, a high frequency of homologous recombination has been seen. An experimental system was used to measure recombination in a vaccinia virus by placing a thymidine kinase (tk) gene between two direct repeats of 1.5 kb of DNA. (Ball, J. Virol. 61:1788-1795, 1987.) During each of the first eight passages under non-selective conditions, 40% of tk+ vaccinia viruses lost their tk+ phenotype. (Id.) Under non-selective conditions, the tk− virus increased to an abundance of 99.73% of the total virus population. (Id.) Even under selective conditions, recombination occurred with such high frequency that the majority of infectious virus particles that could be isolate from single plaques contained DNA that had already undergone recombination with subsequent loss of the tk gene. (Id.) Using a recombinant vaccinia virus designed to express three heterologous genes, all expressed from VV p7.5-promoters, Howley et al., Gene 172:233-237, 1996, demonstrated recombination between the repeated promoter sequences. A vaccinia virus recombinant designed to contain a C-repeat region (CRR) from the M protein of *Streptococcus pyogenes* contained a complex mixture of variants containing from 1 to more than 20 copies of the CRR. (Hruby et al., P.N.A.S. 88:3190-3194, 1991.)

Although it has been shown that multiple genes with homology of about 60-75% inserted into different insertion sites of MVA resulted in a stable multiple recombinant virus (WO 03/097846), there is, however, a need in the art for compositions and methods that reduce the level of intramolecular recombination in vectors, such as, e.g., viral vectors to allow the generation of stable vectors including multiple homologous nucleotide sequences containing longer stretches of identity.

THE INVENTION

The present invention relates to recombinant vectors and methods for making and using them.

In particular, the present invention encompasses a vector comprising two nucleotide sequences of 300 nucleotides in size each coding for 100 amino acids, wherein the 100 amino acids encoded by each of the two nucleotide sequences have at least 75% amino acid identity and wherein one of the two nucleotide sequences has at least 75 nucleotides different from the other nucleotide sequence, wherein the different nucleotides do not alter the identical amino acids encoded by said two nucleotide sequences.

Surprisingly, it was shown according to the present invention that the risk of intramolecular recombination can not only be significantly reduced, but even be avoided by systematically substituting synonymous codons in at least two similar or identical nucleotide sequences within one nucleic acid molecule, such as, for example a vector, thus leading to the generation of stable vectors containing at least two or more similar or identical nucleotide sequences. Unexpectedly, the strategy employed in the present invention is also applicable to vectors containing three or more similar nucleotide sequences.

The results obtained in the present invention show that it is possible to substitute a high number of nucleotides in nucleotide sequences to reduce intramolecular recombination within a vector, while, surprisingly, at the same time expression of the encoded protein is still retained: When introducing a high number of nucleotide variants into long stretches of a nucleotide sequence as was done according to the present invention, the skilled practitioner would have expected that expression of said sequence or gene would not work properly any more, i.e., it was not expected that the changed nucleotide sequence would remain suitable for efficient expression. The strategy employed herein is not only applicable to short nucleotide sequence stretches of 300 nucleotides, but also to much longer stretches as, e.g., full-length genes which, of course, include a stretch of 300 nucleotides as claimed. The results are applicable to many different genes, vectors and viruses and are highly advantageous for vaccine development, such as for example the development of multivalent vaccines, but may also be advantageous for other technologies as, for example, expression of proteins or for the generation of recombinant cell lines.

In other embodiments, the invention also encompasses methods for the generation of viruses and vectors, and methods for reducing intramolecular recombination.

The invention encompasses a method for generating a vector as described above, said method comprising the steps of a) providing a first nucleotide sequence of 300 nucleotides in size coding for 100 amino acids and b) providing a second nucleotide sequence of 300 nucleotides in size coding for 100 amino acids, wherein the 100 amino acids encoded by each of the the two nucleotide sequences have at least 75% amino acid identity and wherein one of the two nucleotide sequences has at least 75 nucleotides different from the other nucleotide sequence, wherein the different nucleotides do not alter the identical amino acids encoded by said two nucleotide sequences; and c) inserting the two divergent nucleotide sequences into a vector.

In a particularly preferred embodiment, the invention encompasses a method for reducing intramolecular recombination within a vector containing two nucleotide sequences of 300 nucleotides in size, each coding for 100 amino acids, wherein the 100 amino acids encoded by each of the two nucleotide sequences have at least 75% amino acid identity, said method comprising substituting nucleotides in one or both nucleotide sequence(s) to generate two divergent sequences which show differences in at least 75 nucleotides, wherein the different nucleotides do not alter the identical amino acids encoded by said two nucleotide sequences.

When using viral vectors, the method reduces the level of intramolecular recombination during each generation of viral propagation. Preferably, the homologous nucleotide sequences recombine in less than 20%, 15%, 10%, 5%, 3%, 2%, 1%, 0.5%, 0.1%, 0.05% or 0.01%. of the progeny viruses per generation.

In another preferred embodiment, the invention encompasses a method for generating a virus, preferably a poxvirus, comprising two homologous nucleotide sequences, said method comprising the steps of a) providing a virus comprising a nucleotide sequence of 300 nucleotides in size coding for 100 amino acids and b) inserting a second nucleotide sequence of 300 nucleotides in size coding for 100 amino acids into the virus; wherein the 100 amino acids encoded by each of the two nucleotide sequences have at least 75% amino acid identity, and wherein one of the two nucleotide sequences has at least 75 nucleotides different from the other nucleotide sequence, wherein the different nucleotides do not alter the identical amino acids encoded by said two nucleotide sequences.

As used herein, a "vector" may be any agent capable of delivering and expressing nucleic acid molecules in a host cell or subject. Thus, a vector may be a PCR product or any piece of nucleic acid introduced into a cell and/or integrated in the cellular genome; or a replicon, such as a plasmid, phage, or cosmid, into which another DNA segment may be inserted so as to bring about the replication of the inserted segment. Generally, a vector may replicate when associated with the proper control elements. Suitable vector backbones for use in the present invention include, for example, those routinely used in the art such as plasmids, viruses, artificial chromosomes, BACs, YACs, or PACs or even recombinant cells like bacteria and eukaryotic cells. The term "vector" includes cloning and expression vectors, as well as viral vectors and integrating vectors. An "expression vector" is a vector that includes a regulatory region. Suitable expression vectors for use in the present invention include, without limitation, plasmids and viral vectors derived from, for example, plant viruses, bacteriophage, baculoviruses, tobacco mosaic virus, retroviruses, and poxviruses. Suitable non viral vectors include plasmids such as pREP4, pCEP4 (Invitrogene), pCI (Promega), pCDM8 (Seed, 1987, Nature 329, 840), pVAX and pgWiz (Gene Therapy System Inc; Himoudi et al, 2002, J. Virol. 76, 12735-12746). Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

In vaccine development, a recombinant virus can be used as the vehicle or vaccine vector for delivering genetic material to a cell. Once in the cell, genetic information is transcribed and translated into proteins, including the inserted antigen targeted against a specific disease. Treatment is successful if the antigen delivered by the vector into the cell induces the body's immune response against the antigen that protects against the disease.

In a preferred embodiment of the present invention, the vector is a plasmid or a viral vector.

A viral vector can be based on an attenuated virus, which cannot replicate in the host, but is able to introduce and express a foreign gene in the infected cell. The virus or the recombinant virus is thereby able to make a protein and display it to the immune system of the host. Some key features of viral vectors are that they can elicit a humoral (B-cell) and/or cell-mediated (T-cell) immune response.

Viral vectors may be obtained from a variety of different viruses. In one embodiment, the virus is an animal virus. The vector may be obtained especially from a virus selected from the group consisting of retrovirus, picornavirus, influenza virus, adenovirus, adeno-associated virus (AAV), poxvirus, herpes virus (e.g., HSV-1), measles virus and foamy virus.

Viral vectors are commonly used by researchers to develop vaccines for the prevention and treatment of infectious diseases and cancer. Of these, poxviruses (including canary pox, vaccinia, and fowl pox) are belonging to the group of the most common vector vaccine candidates. Poxviruses are a preferred choice for transfer of genetic material into new hosts due to the relatively large capacity for insertion of sequences into the viral genome and because of their ability to replicate their genomes and perform transcription in the infected cell's cytoplasm instead of the nucleus, thereby minimizing the risk of insertional mutagenesis by integrating genetic material into the genome of the host cell as seen with other vectors, e.g. retroviral vectors. The virions of poxviruses are large as compared to most other animal viruses (for more details see Fields et al., eds., Virology, 3rd Edition, Volume 2, Chapter 83, pages 2637 ff).

In a preferred embodiment of the invention, the viral vector is derived from a poxvirus (see for example Cox et al. in "Viruses in Human Gene Therapy" Ed J. M. Hos, Carolina Academic Press). It may be obtained from any member of the poxviridae and may be, in particular an avipoxvirus or an orthopoxvirus.

Examples for avipoxviruses suitable for use in the present invention include any avipoxvirus such as Fowlpoxvirus, Canarypoxvirus, Uncopoxvirus, Mynahpoxvirus, Pigeonpoxvirus, Psittacinepoxvirus, Quailpoxvirus, Peacockpoxvirus, Penguinpoxvirus, Sparrowpoxvirus, Starlingpoxvirus and Turkeypoxvirus. Preferred avipoxviruses are Canarypoxvirus and Fowlpoxvirus.

Avipoxviruses are naturally host-restricted and productively replicate only in avian species and cells (Taylor et al., Biological and immunogenic properties of a canarypox-rabies recombinant, ALVAC-RG (vCP65) in non-avian species, Vaccine 13: 539-549, 1995). If human cells are infected with an avipoxvirus, heterologous genes are expressed from the viral genome. However, the avipoxvirus does not fully replicate in the human cells and there is, thus, no risk that the human being is harmed by productive virus replication. Various recombinant avipoxviruses have been constructed that express e. g. lentiviral gene products (U.S. Pat. No. 5,766,598), cytokines and/or tumor-associated antigens (U.S. Pat. No. 5,833,975) or rabies G glycoprotein (Taylor et al., Biological and immunogenic properties of a canarypox-rabies recombinant, ALVAC-RG (vCP65) in non-avian species, Vaccine 13: 539-549, 1995). A recombinant canarypox virus expressing the four HIV genes gag, pol, env and nef has already been used in clinical trials (Peters, B. S., The basis for HIV immunotherapeutic vaccines, Vaccine 20: 688-705, 2001).

Since avipoxviruses productively replicate only in avian cells, these cells have to be used for the amplification of the virus and for the generation of recombinant viruses.

An example for a canarypox virus is strain Rentschler. A plaque purified Canarypox strain termed ALVAC (U.S. Pat. No. 5,766,598) was deposited under the terms of the Budapest treaty with the American Type Culture Collection (ATCC), accession number VR-2547. Another Canarypox strain is the commercial canarypox vaccine strain designated LF2 CEP 524 24 10 75, available from Institute Merieux, Inc.

Examples of a Fowlpox virus are strains FP-1, FP-5 and TROVAC (U.S. Pat. No. 5,766,598). FP-1 is a Duvette strain modified to be used as a vaccine in oneday old chickens. The strain is a commercial fowlpox virus vaccine strain designated 0 DCEP 25/CEP67/2309 October 1980 and is available from Institute Merieux, Inc. FP-5 is a commercial fowlpox virus vaccine strain of chicken embryo origin available from American Scientific Laboratories (Division of Schering Corp.) Madison, Wis., United States Veterinary License No. 165, serial No. 30321.

Of the poxviruses, the vaccinia and variola species are the two best known. Variola virus is the cause of smallpox. In contrast to variola virus, vaccinia virus does not normally cause systemic disease in immune-competent individuals and it has therefore been used as a live vaccine to immunize against smallpox. Successful worldwide vaccination with vaccinia virus culminated in the eradication of smallpox as a natural disease in the 1980s (The global eradication of smallpox. Final report of the global commission for the certification of smallpox eradication; History of Public Health, No. 4, Geneva: World Health Organization, 1980). Since then, vaccination has been discontinued for many years, except for people at high risk of poxvirus infections (for example, laboratory workers). However, there is an increasing fear that, for example, variola causing smallpox may be used as a bio-terror weapon. Furthermore, there is a risk that other poxviruses such as cowpox, camelpox, and monkeypox may potentially mutate, through selection mechanisms, and obtain similar phenotypes as variola. Several governments are therefore building up stockpiles of vaccinia-based vaccines to be used either pre-exposure (before encounter with variola virus) or post-exposure (after encounter with variola virus) of a presumed or actual smallpox attack.

In a particular preferred embodiment of the invention, the vector is a vaccinia virus vector.

Vaccinia virus is highly immune-stimulating and provokes strong B- (humoral) and T-cell mediated (cellular) immunity to both, its own gene products and to many foreign gene product expressed from genes inserted in the vaccinia genome. Vaccinia virus is, therefore, seen as an ideal vector for vaccines against smallpox and other infectious diseases and cancer in the form of recombinant vaccines. Many of the recombinant vaccinia viruses described in the literatur are based on the fully replication competent Western Reserve strain of Vaccinia virus. However, it is known that this strain has a high neurovirulence and is, thus, poorly suited for use in humans and animals (Morita et al. 1987, Vaccine 5, 65-70).

A suitable vaccinia virus can be selected from the group consisting of the Copenhagen strain (Goebel et al., 1990, Virol. 179, 247-266 and 517-563; Johnson et al., 1993, Virol. 196, 381-401), the Wyeth strain, NYVAC (see WO92/15672 and Tartaglia et al., 1992, Virology 188, 217-232) and the highly attenuated modified Ankara (MVA) strain (Mayr et al., 1975, Infection 3, 6-16).

A preferred example of a suitable vaccinia virus is the highly attenuated vaccinia virus strain NYVAC, which was derived from a plaque-cloned isolate of the Copenhagen vaccine strain by deletion of 18 ORFs from the viral genome (Tartaglia et al., NYVAC: A highly attenuated strain of vaccinia virus, Virology 188, 217-232, 1992). NYVAC is characterized by a dramatically reduced ability to replicate on a variety of human tissue culture cells, but retains the ability to induce strong immune responses to extrinsic antigens.

All of the above-described viruses are equally suitable for use in the present invention.

In a most preferred embodiment of the invention, the virus is a modified vaccinia virus Ankara (MVA) which is known to be exceptionally safe in vaccinations.

Modified Vaccinia virus Ankara (MVA) virus is related to Vaccinia virus, a member of the genus Orthopoxvirus in the family Poxviridae. MVA has been generated by 516 serial passages on chicken embryo fibroblasts of the dermal vaccinia strain Ankara (Chorioallantois vaccinia virus Ankara, CVA) (for review see Mayr, A., et al., Passage History:

Abstammung, Eigenschaften and Verwendung des attenuierten Vaccinia-Stammes MVA, Infection 3, 6-14, 1975). As a consequence of these long-term passages the resulting MVA virus deleted about 31 kilobases of its genomic sequence and, therefore, was described as highly host cell restricted to avian cells (Meyer, H. et al., Mapping of deletions in the genome of the highly attenuated vaccinia virus MVA and their influence on virulence, J. Gen. Virol. 72, 1031-1038, 1991; (Meisinger-Henschel et al., Genomic sequence of chorioallantois vaccinia virus Ankara, the ancestor of modified vaccinia virus Ankara, J. Gen. Virol. 88, 3249-3259, 2007). It was shown, in a variety of animal models that the resulting MVA was significantly avirulent (Mayr, A. & Danner, K. Vaccination against pox diseases under immunosuppressive conditions, Dev. Biol. Stand. 41: 225-34, 1978). Additionally, this MVA strain has been tested in clinical trials as vaccine to immunize against the human smallpox disease (Mayr et al., Zbl. Bakt. Hyg. I, Abt. Org. B 167, 375-390 [1987], Stickl et al., MVA vaccination against smallpox: clinical tests with an attenuated live vaccinia virus strain (MVA) (author's transl), Dtsch. med. Wschr. 99, 2386-2392, 1974). These studies involved over 120,000 humans, including high risk patients, and proved that, compared to Vaccinia based vaccines, MVA had diminished virulence or infectiousness while it maintained good immunogenicity.

The invention encompasses recombinant MVA viruses generated with any and all MVA viruses. An example for an MVA strain is deposit VR-1508, deposited at the American Type Culture collection (ATCC), Manassas, Va. 20108, USA. In another embodiment the MVA-Vero strain or a derivative thereof can be used according to the present invention. The strain MVA-Vero has been deposited at the European Collection of Animal Cell Cultures under the deposition number ECACC V99101431 and ECACC 01021411. Further examples for MVA virus strains used according to the present invention are strains MVA 572 and 575 deposited at the European Collection of Animal Cell Cultures (ECACC), Salisbury (UK) with the deposition number ECACC V94012707 and ECACC V00120707, respectively. Particularly preferred MVA viruses are MVA variant strains MVA-BN® as, e.g., deposited at ECACC under number V00083008, and derivatives having the same properties as MVA-BN®.

MVA-BN® is a virus used in the manufacturing of a stand-alone third generation smallpox vaccine. MVA-BN® was developed by further passages from MVA strain 571/572. To date, more than 1500 subjects including subjects with atopic dermatitis (AD) and HIV infection have been vaccinated in clinical trials with MVA-BN® based vaccines.

Derivatives having the same properties as the deposited strain of MVA-BN® have the capability of reproductive replication in vitro in chicken embryo fibroblasts (CEF), but no capability of reproductive replication in human cells in which MVA 575 or MVA 572 can reproductively replicate. Most preferably, the MVA has no capability of reproductive replication in the human keratinocyte cell line HaCaT, the human embryo kidney cell line 293, the human bone osteosarcoma cell line 143B, and the human cervix adenocarcinoma cell line HeLa.

The term "not capable of reproductive replication" is used in the present application as defined in WO 02/42480 and U.S. Pat. No. 6,761,893, respectively. Thus, said term applies to a virus that has a virus amplification ratio at 4 days after infection of less than 1 using the assays described in U.S. Pat. No. 6,761,893, which assays are hereby incorporated by reference. The "amplification ratio" of a virus is the ratio of virus produced from an infected cell (Output) to the amount originally used to infect the cells in the first place (Input). A ratio of "1" between Output and Input defines an amplification status wherein the amount of virus produced from the infected cells is the same as the amount initially used to infect the cells.

In a most preferred embodiment, the MVA strain used in the present invention is MVA-BN® or a derivative as described above. The features of MVA-BN®, the description of biological assays allowing evaluating whether an MVA strain is MVA-BN® or a derivative thereof and methods allowing to obtain MVA-BN® or an MVA having the properties of MVA-BN® are disclosed in WO 02/42480. The content of this application is included in the present application by reference. The highly attenuated MVA-BN® virus can be derived, e.g., by the further passage of a modified vaccinia virus Ankara (MVA), such as MVA-572 or MVA-575 and, optionally, by plaque or clone purification. MVA-BN® lacks approximately 13% (26.5 kb from six major and multiple minor deletion sites) of the genome compared with ancestral CVA virus. The deletions affect a number of virulence and host range genes, as well as a large fragment of the gene coding for A-type inclusion protein (ATI) and a gene coding for a structural protein directing mature virus particles into A-type inclusion bodies.

In particular, reference is made to the definition of the properties of the MVA according to the invention as described in WO 02/42480, such as the properties of MVA-BN® and the properties and definitions of the derivates of MVA-BN®. Said reference also discloses how MVA and other vaccinia viruses can be propagated. Briefly, eukaryotic cells are infected with the virus. The eukaryotic cells are cells that are susceptible to infection with the respective poxvirus and allow replication and production of infectious virus. For MVA an example for this type of cells are chicken embryo fibroblasts (CEF) and BHK cells (Drexler et al., Highly attenuated modified vaccinia Ankara replicates in baby hamster kidney cells, a potential host for virus propagation, but not in various human transformed and primary cells, J. Gen. Virol. 79, 347-352, 1998). CEF cells can be cultivated under conditions known to the person skilled in the art. Preferably the CEF cells are cultivated in serum-free medium in stationary flasks or roller bottles. The incubation preferably takes place 48 to 96 hours at 37° C. For the infection MVA is preferably used at a multiplicity of infection (MOI) of 0.05 to 1 $TCID_{50}$ and the incubation preferably takes place 48 to 72 hours at 37° C.

The viruses as used according to the invention can be propagated on various cell cultures, particularly animal cell cultures. The virus is allowed to infect susceptible cell cultures and reproductively replicate. Progeny viruses are collected by routine techniques in the art.

For example, with MVA viruses and other vaccinia viruses, chicken embryo fibroblasts (CEFs) in serum-containing or serum-free medium can be infected with the viruses. After the virus has been allowed to reproductively replicate, progeny viruses are collected.

The present invention also relates to a recombinant poxvirus, preferably vaccinia virus, in particular MVA, capable of expressing two or more homologous nucleotide sequences, in particular coding sequences. The virus can contain two, three, four or more homologous nucleotide coding sequences.

The vector of the present invention comprises two nucleotide sequences of 300 nucleotides in size. In a preferred embodiment, the vector comprises three, four, five, six or more nucleotide sequences, which, of course, encompass also two nucleotide sequences as claimed. 300 nucleotides may, of course, also be part of a longer nucleotide sequence.

Additionally, in various embodiments, the two or more nucleotide sequences are 300, 350, 400, 450, 500, 600, 700, 800, 900, 1000, 1500, 2000, 2500, or 3000 or even more nucleotides in size which may all be part of longer nucleotide sequences and which, of course, all include 300 nucleotides as claimed.

As used herein, the terms "polynucleotide", "nucleotide sequence", "nucleic acid", "nucleic acid molecule" "nucleic acid sequence" are used interchangeable and define a polymer of either polydeoxyribonucleotides (DNA) or polyribonucleotides (RNA) molecules or any combination thereof. The definition encompasses single or double-stranded, linear or circular, naturally occurring or synthetic polynucleotides.

The nucleotide sequences of the present invention may be coding sequences and can contain complete genes, respectively. The term "coding sequence", as used herein, refers to a nucleotide sequence that codes for a specific amino acid sequence. Non-coding sequences of genes include introns and control regions, such as promoters, operators, and terminators.

The nucleotide sequences can also contain gene fragments. The nucleotide sequences can contain synthetic sequences, such as nucleotide sequences encoding amino acid linker sequences or epitopes. The nucleotide sequences can be composed of a mixture of genes, gene fragments, and synthetic sequences. The nucleotide sequence may also contain analogs such as nucleotide analogs, phosphate ester analog and/or pentose sugar analog. Also included within the definition of nucleotide analogs are nucleotides in which the phosphate ester and/or sugar phosphate ester linkages are replaced with other types of linkages, such as N-(2-aminoethyl)-glycine amides and other amides (see, e.g., Nielsen et al., 1991, Science 254: 1497-1500; WO 92/20702; U.S. Pat. No. 5,719,262; U.S. Pat. No. 5,698,685); morpholinos (see, e.g., U.S. Pat. No. 5,698,685; U.S. Pat. No. 5,378,841; U.S. Pat. No. 5,185,144); carbamates (see, e.g., Stirchak & Summerton, 1987, J. Org. Chem. 52: 4202); methylene(methylimino) (see, e.g., Vasseur et al., 1992, J. Am. Chem. Soc. 114: 4006); 3'thioformacetals (see, e.g., Jones et al., 1993, J. Org. Chem. 58: 2983); sulfamates (see, e.g., U.S. Pat. No. 5,470,967); 2-aminoethylglycine, commonly referred to as PNA (see, e.g., Buchardt, WO 92/20702; Nielsen (1991) Science 254:1497-1500); and others (see, e.g., U.S. Pat. No. 5,817,781; Frier & Altman, 1997, Nucl. Acids Res. 25:4429 and the references cited therein). Phosphate ester analogs include, but are not limited to, (i) C1-C4 alkylphosphonate, e.g. methylphosphonate; (ii) phosphoramidate; (iii) C1-C6 alkyl-phosphotriester; (iv) phosphorothioate; and (v) phosphorodithioate.

Further modifications include chemical modifications (e.g. see WO 92/03568; U.S. Pat. No. 5,118,672) in order to increase the in vivo stability of the nucleic acid, enhance the delivery thereof, or reduce the clearance rate from the host subject.

Furthermore, in one embodiment, the nucleotide sequence can contain fusion genes, artificial genes and polyepitopes.

A fusion gene, as denoted herein, is a hybrid gene formed from two previously separate genes, gene fragments or artificial DNA or epitopes. It can occur as the result of a translocation, interstitial deletion, or inversion.

A fusion gene can be constructed by linking at least two DNA fragments, wherein the DNA fragments encode identical or different amino acid sequences Fusion proteins may facilitate the expression and/or purification of proteins. For example, a polypeptide of the invention may be generated as a glutathione-S-transferase (GST) fusion protein. Such GST fusion proteins may be used to simplify purification of a polypeptide of the invention, such as through the use of glutathione-derivatized matrices (see, for example, Current Protocols in Molecular Biology, eds. Ausubel et al., (N.Y.: John Wiley & Sons, 1991)). In another embodiment, a fusion gene coding for a purification leader sequence, such as a poly-(His)/enterokinase cleavage site sequence at the N-terminus of the desired portion of the recombinant protein, may allow purification of the expressed fusion protein by affinity chromatography using a Ni2+ metal resin. The purification leader sequence may then be subsequently removed by treatment with enterokinase to provide the purified protein (e.g., see Hochuli et al., (1987) J. Chromatography 411: 177; and Janknecht et al., PNAS USA 88:8972). Further heterologous sequences encoding a polypeptide permitting the detection, isolation, solubilization and/or stabilization of the polypeptide to which it is fused, include poly His tag, myc, HA, protein A, protein G, calmodulin-binding peptide, thioredoxin, maltose-binding protein, poly arginine, poly His-Asp, FLAG, a portion of an immunoglobulin protein, and a transcytosis peptide.

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene may be synthesized by conventional techniques including automated DNA synthesizers. Alternatively, PCR amplification of gene fragments may be carried out using anchor primers which give rise to complementary overhangs between two consecutive gene fragments which may subsequently be annealed to generate a chimeric gene sequence (see, for example, Current Protocols in Molecular Biology, eds. Ausubel et al., John Wiley & Sons: 1992) and by fusion PCR wherein two or more polynucleotides are sharing a stretch of identity, which in a PCR reaction can result in fused polynucleotide sequences.

In another preferred embodiment, the nucleotide sequence of the present invention encodes a polyepitope. A polyepitope is a chimeric protein containing isolated epitopes from at least one protein/antigen, preferably from more than one protein/antigen.

Said epitopes can be "isolated" or "biologically pure". The term "isolated" refers to material that is substantially free from components that normally accompany it as found in its naturally occurring environment. An "isolated" epitope refers to an epitope that does not include the neighbouring amino acids of the whole sequence of the antigen or protein from which the epitope was derived.

With regard to a particular amino acid sequence, an "epitope" is a set of amino acid residues which is involved in recognition by a particular immunoglobulin, or in the context of T cells, those residues necessary for recognition by T cell receptor proteins and/or Major Histocompatibility Complex (MHC) molecules. The term "peptide" designates a series of amino acids, connected one to the other, typically by peptide bonds between the amino and carboxyl groups of adjacent amino acids.

The epitopes are of a certain length and bind to a molecule functioning in the immune system, preferably a HLA class I and a T-cell receptor. The epitopes in a polyepitope construct can be HLA class I epitopes and optionally HLA class II epitopes. HLA class I epitopes are referred to as CTL epitopes and HLA class II epitopes are referred to as HTL epitopes. Some polyepitope constructs can have a subset of HLA class I epitopes and another subset of HLA class II epitopes. A CTL epitope usually consists of 13 or less amino acid residues in length, 12 or less amino acids in length, or 11 or less amino acids in length, preferably from 8 to 13 amino acids in length, most preferably from 8 to 11 amino acids in length (i.e. 8, 9, 10, or 11). A HTL epitope consists of 50 or less amino acid residues in length, and usually from 6 to 30 residues, more usually from 12 to 25, and preferably consists of 15 to 20 (i.e. 15, 16, 17, 18, 19, or 20) amino acids in length. The polyepitope construct of the present invention preferably includes 2 or more, 5 or more, 10 or more, 13 or more, 15 or more, 20 or more, or 25 or more CTL epitopes. More specific, the polyepitope construct comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60 or more CTL epitopes.

The homologous nucleotide sequences according to the present invention can be derived from any organism, microorganism, such as any virus, any bacterium, any fungus or parasite. The homologous nucleotide sequences can be either heterologous to the sequence of the vector, but also homologous thereto: When, for example, a virus is used as a vector, also viral own nucleotide sequences can be multiplied according to the present invention, for example, in order to overexpress a protein of the virus for getting enhanced immune reactivity or safety. Preferably, the homologous nucleotide sequences are derived from an infectious or pathogenic microorganism and most preferably from different strains or clades, variants, subtypes or serotypes of said microorganism. The terms "strain" or "clade" are technical terms, well known to the practitioner, referring to the taxonomy of microorganisms. The taxonomic system classifies all so far characterised microorganisms into the hierarchic order of Families, Genera, Species, Strains (Fields Virology, ed. by Fields B. N., Lippincott-Raven Publishers, 4th edition 2001). While the criteria for the members of Family is their phylogenetic relationship, a Genera comprises all members which share common characteristics, and a Species is defined as a polythetic class that constitutes a replicating lineage and occupies a particular ecological niche. The term "strain" or "clade" describes a microorganism, i. e. virus, which shares the common characteristics, like basic morphology or genome structure and organisation, but varies in biological properties, like host range, tissue tropism, geographic distribution, attenuation or pathogenicity. The term "variants" or "serotypes" further distinguishes between members of the same strain, also called subtypes, which show individual infection spectra or antigenic properties due to minor genomic variations.

According to a further embodiment of the present invention the homologous nucleotide sequences are preferably selected from viruses. Representative examples of viruses include without limitation HIV (HIV-I or HIV-2), herpes viruses (e.g. HSVI or HSV2), cytomegalovirus (CMV), Epstein Barr virus (EBV), hepatitis viruses (e.g. hepatitis A virus (HAV), HBV, HCV and hepatitis E virus), flaviviruses (e.g. Yellow Fever Virus), varicella-zoster virus (VZV), paramyxoviruses, respiratory syncytial viruses (RSV), parainfluenza viruses, measles virus, influenza viruses, and papillomaviruses.

According to another embodiment, the homologous nucleotide sequences are selected from Dengue virus genes. Most preferred are homologous genes derived from different serotypes of the virus, wherein said genes may be derived from one, two, three or from all of the 4 Dengue virus serotypes.

In a preferred embodiment, the two homologous nucleotide sequences encode respiratory syncitial virus (RSV) genes. In a preferred embodiment, the homologous nucleotide sequences encode RSV-F and/or RSV-G proteins. Preferably, one of the RSV genes is full-length and the other is truncated.

In another preferred embodiment, the two, preferably three homologous nucleotide sequences encode Ebola virus (EBOV) proteins. Three homologous nucleotide sequences encoding Ebola virus (EBOV) proteins do, of course, also cover two homologous nucleotide sequences. In a preferred embodiment, the homologous nucleotide sequences encode EBOV glycoproteins (GP). In a particular preferred embodiment, the nucleotide sequences encode glycoprotein precursor proteins from the EBOV strains EBOV-B (Bundibugyo), EBOV-S (Sudan ebolavirus strain Gulu) and EBOV-Z (Zaire ebola virus strain Mayinga).

In another embodiment, the homologous nucleotide sequences are selected from bacteria. Representative examples of suitable bacteria include without limitation *Neisseria* (e.g. *N. gonorrhea* and *N. meningitidis*); *Bordetella* (e.g. *B. pertussis*, *B. parapertussis* and *B. bronchiseptica*), *Mycobacteria* (e.g. *M. tuberculosis*, *M. bovis*, *M. leprae*, *M. avium*, *M. paratuberculosis*, *M. smegmatis*); *Legionella* (e.g. *L. pneumophila*); *Escherichia* (e.g. enterotoxic *E. coli*, enterohemorragic *E. coli*, enteropathogenic *E. coli*); *Shigella* (e.g. *S. sonnei*, *S. dysenteriae*, *S. flexnerii*); *Salmonella* (e.g. *S. typhi*, *S. paratyphi*, *S. choleraesuis*, *S. enteritidis*); *Listeria* (e.g. *L. monocytogenes*); *Helicobacter* (e.g. *H. pylori*); *Pseudomonas* (e.g. *P. aeruginosa*); *Staphylococcus* (e.g. *S. aureus*, *S. epidermidis*); *Enterococcus* (e.g. *E. faecalis*, *E. faecium*); *Bacillus* (e.g. *B. anthracis*); *Corynebacterium* (e.g. *C. diphtheriae*), and *Chlamydia* (e.g. *C. trachomatis*, *C. pneumoniae*, *C. psittaci*). Representative examples of parasites include without limitation *Plasmodium* (e.g. *P. falciparum*); *Toxoplasma* (e.g. *T. gondii*); *Leshmania* (e.g. *L. major*); *Pneumocystis* (e.g. *P. carinii*); and *Schisostoma* (e.g. *S. mansoni*). Representative examples of fungi include without limitation *Candida* (e.g. *C. albicans*) and *Aspergillus*.

The at least two nucleotide sequences can be of the same size or of different sizes. In a preferred embodiment, one of the two nucleotide sequences is truncated relative to the other. The truncation can be at the 5' or 3' end.

In various embodiments, the 300 nucleotides of the two nucleotide sequences encode 100 amino acids, which have at least 75%, 80%, 85%, 90%, 95%, 98%, 99%, or 100% amino acid identity. In a preferred embodiment, said amino acid identity is within a stretch of 100, 125, 150, 175, 200, 250, 300, 350, 400, 450, 500, 600, 700, 800, 900 or 1000 or more contiguous amino acids.

In a particular preferred embodiment, the amino acids have at least 75%, 80%, 85%, 90%, 95%, 98%, 99%, or 100% amino acid identity within a stretch of at least 150 or 200 contiguous amino acids.

In other preferred embodiments, the proteins encoded by the two nucleotide sequences have at least 75%, 80%, 85%, 90%, 95%, 98%, 99%, or 100% amino acid identity within a stretch of 300 or 500 contiguous amino acids. In other preferred embodiments, the proteins encoded by the at least two nucleotide sequences have 85%-100%, in particular 100% amino acid identity within a stretch of 100, 200, 400, 600, or 800 contiguous amino acids in pairwise comparison.

As used herein, any term referring to "percent sequence identity", such as "amino acid identity" refers to the degree of identity between any given query sequence and a subject sequence.

Specifically, the following terms are used to describe the sequence relationships between two or more nucleic acids, polynucleotides or amino acid sequences: "reference sequence", "comparison window", "sequence identity", "percentage of sequence identity", and "substantial identity". A "reference sequence" is a defined sequence used as a basis for a sequence comparison; a reference sequence may be a subset of a larger sequence.

The terms "identical" or percent "identity," in the context of two or more nucleic acids or polypeptide sequences, refer to two or more sequences or subsequences that are the same or have a specified percentage of amino acid residues or nucleotides that are the same (e.g., 75% identity, 80% identity, 85% identity, 90% identity, 99%, or 100% identity in pairwise comparison), when compared and aligned for maximum correspondence over a comparison window, or designated region as measured using a sequence comparison algorithm or by manual alignment and visual inspection. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity.

The phrase "substantially identical", in the context of two nucleic acids or polypeptides, refers to two or more sequences or subsequences that have at least about 85%, identity, at least about 86%, 87%, 88%, 89%, 90%, 91%, 92%, 93%, 94%, 95%, 96%, 97%, 98%, 99%, or 100% nucleotide or amino acid residue identity, when compared and aligned pairwise for maximum correspondence, as measured using a sequence comparison algorithm or by visual inspection. In an exemplary embodiment, the substantial identity exists over a region of the sequences that is at least about 50 residues in length. In another exemplary embodiment, the substantial identity exists over a region of the sequences that is at least about 100 residues in length. In still another exemplary embodiment, the substantial identity exists over a region of the sequences that is at least about 150 residues or more, in length. In one exemplary embodiment, the sequences are substantially identical over the entire length of nucleic acid or protein sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually 20 to 50, about 50 to about 100, about 100 to about 200, more usually about 100 to about 150, or of about 20, 50, 100, 150, 200, 250, 300, 350, 400, 450, 500, 600, 700, 800, 900, 1000, 1500, 2000, 2500, or 3000 or even more in which a sequence may be compared to a reference sequence of the same number of contiguous positions after the two sequences are optimally aligned.

Percent identity can be determined using the alignment method of Needleman and Wunsch (J. Mol. Biol. 48; 443-453 (1970)) that has been shown to be equivalent to Sellers (SIAM J. of Applied Math 26; 787-793 (1974). The percent identity may be determined, for example, by comparing sequence information using the GAP computer program, version 6.0 described by Devereux et al. (Nucl. Acids Res. 12:387, 1984) and available from the University of Wisconsin Genetics Computer Group (UWGCG), which utilizes this alignment method. The preferred default parameters for the GAP program include: (1) a unary comparison matrix (containing a value of 1 for identities and 0 for non-identities) for nucleotides, and the weighted comparison matrix of Gribskov and Burgess, Nucl Acids Res. 14:6745, 1986, as described by Schwartz and Dayhoff, eds., Atlas of Protein Sequence and Structure, National Biomedical Research Foundation, pp. 353-358, 1979; (2) a penalty of 3.0 for each gap and an additional 0.10 penalty for each symbol in each gap; and (3) no penalty for end gaps. Another suitable tool is to use the ContigExpress from the VectorNTI Advance program (INVITROGEN), e.g. version 10.3.1 from 2007.

According to the present invention, the degeneracy of the genetic code is used to make homologous or identical nucleotide sequences less homologous in order to prevent intramolecular recombination. Said differences may already be included in the nucleotide sequences by nature and/or are included artificially by substitutions. In various embodiments, the number of different nucleotides originating from nature plus from artificial substitution is at least 75, 80, 85, 90, 95, 100, 125, 150, 175, 200, 250, 300, 350, 400, 450, or 500. Preferably, the number of different bases is at least 75, 200 or 450. The number of differences does, of course, vary and increase, respectively, with the number of nucleotides of the nucleotide sequences.

In a preferred embodiment, at least 75, 80, 85, 90, 95, 100, 125, 150, 175, 200, 250, 300, 350, 400, 450, or 500 nucleotides are substituted. Said substitutions are artificially introduced independently of already present numbers of different nucleotides included, for example, by silent mutations.

In various embodiments, two nucleotide sequences with stretches of identity of no more than 13, 12, 11, 10, 9, 8, 7, 6, 5, or 4 contiguous nucleotides after substitution are preferred. In case of more than two nucleotide sequences, stretches of identity of no more than 20, 19, 18, 17, 16, 15, 14, 13, 12, 11, 10, 9, 8, 7, 6, 5 or 4 contiguous nucleotides after subsitlution are preferred.

In another embodiment, the nucleotide sequences can have at least 75, 100, 150, 200, 250, 300, 350, 400, or 450 nucleotides substituted out of 300, 400, 500, 600, 700, 800, 900, 100, 1100, 1200, 1300, 1400, 1500, or 1600 or more nucleotides.

In the context of this invention, substitution of nucleotides with different nucleotides means the technical or artificial replacement of nucleotides by other nucleotides. Preferably, the substituted nucleotides do not alter the encoded amino acid sequence. Substitution can be performed by identifying codons in the two homologous nucleotide sequences encoding the same amino acids and altering codons in one of the two homologous nucleotide sequences such that the codons still encodes the same amino acids. The alterations can be made in one, both or all of the homologous nucleotide sequences.

For example the amino acid proline is encoded by the codons CCA, CCC, CCG and CCU (on the DNA level the U is replaced by a T). A simple nucleotide sequence, CCCCCC, initially encoding two prolines in two homologous nucleotide sequences could be changed to CCACCG, also encoding two prolines, in one of the two homologous nucleotide sequences. Alternatively, one of the sequences encoding proline-proline could be changed to CCCCCG, and the other to CCACCC.

A more complicated example is the amino acid serine, which is encoded by UCA, UCC, UCG, UCU, AGC and AGU. Similarly, UCAUCA, initially encoding two different serines could be changed in multiple homologous sequences, to AGCAGC (sharing no common nucleotide with UCAUCA) and UCGAGU (sharing only one position with UCAUCA or two position with AGCAGC) and so on. This allows a higher flexibility in introducing different nucleotide variants into two or more nucleotide sequences encoding a serine-serine.

Preferably codon optimization as described in the present invention avoids the use of rare codons for a desired host since rare codons may block or reduce expression of the encoded protein. Also, substitutions that may introduce nucleic acid signals for the desired host are preferably avoided. Such signals include, but are not limited to, splice signals, termination signals, and initiation signals. Preferably, the following sequence motifs may be avoided depending on the type of vector used, e.g., the vaccinia virus early transcription termination signal needs not to be avoided in many other vectors, being no poxvirus vectors:

internal TATA-boxes, chi-sites, and ribosomal entry sites;
AT-rich and GC-rich sequence stretches;
ARE, INS, and CRS sequence elements;
repeat sequences and RNA secondary structures;
(cryptic) splice donor and acceptor sites, and branch points; and
vaccinia early transcription termination signals: (TTTTTNT).

BRIEF DESCRIPTION OF THE DRAWINGS

The invention is more fully understood with reference to the drawings, in which:

FIG. 1 depicts an alignment of the nucleotide sequence encoding the full-length RSV-F (F) protein (SEQ ID NO:1) with the nucleotide sequence encoding the substituted, truncated RSV-F_trunc (F_trunc) protein (SEQ ID NO:2). The identical sequences are highlighted in black, and the substituted nucleotides remain unhighlighted. The locations of primers A1 and B2 are indicated.

FIG. 2 depicts an alignment of the full-length RSV-F (F) protein (SEQ ID NO:3) with the truncated RSV-F_trunc (F_trunc) protein (SEQ ID NO:4). The full length sequence of RSV-F is truncated by 50 aa to result in the truncated RSV-F_trunc protein. The RSV-F_trunc protein covers approximately 91% of the full length protein.

FIGS. 5A-C depict the hypothetical recombination F/F$_{trunc}$ between the full lengthRSV-F gene (F) and the truncated F gene (F$_{trunc}$) in the double recombinant MVA and the locations of the PCR primers in the recombinant and non-recombinant viruses and control plasmids. A. MVA-mBN175B. B. pMISC173. C. pMISC172.

FIG. 7 depicts an alignment of three EBOV (ebolavirus) GP (glycoprotein) protein sequences. The amino acid sequences of three GP proteins of the ebola virus strains EBOV-B (SEQ ID NO:5), EBOV-S (SEQ ID NO:6) and EBOV-Z (SEQ ID NO:7) are aligned. No gaps were allowed in the alignment. The overall identity in all three protein sequences is 48.5%. Gray background: identical in all three protein sequences. Black background: identical in two proteins.

FIGS. 8A and 8B depict an alignment of three EBOV GP coding sequences used in the recombinant MVA-BN® based construct. The coding sequences for the GP genes originating from three EBOV strains EBOV-B (SEQ ID NO:8), -S (SEQ ID NO:9) and -Z (SEQ ID NO:10) were aligned before (non-opt; see FIG. 8A, (SEQ ID NOs:8-10)) and after (opt; see FIG. 8B, (SEQ ID NOs:11-13)) optimization. No gaps were allowed in the alignment. Gray background: identical nucleotide positions in three coding sequences. Black background: identical nucleotide positions in two coding sequences. The identity in nucleotide positions of three genes prior optimization (non-opt) is 45.3%, while after optimization (opt) it is 44.6%.

FIGS. 9A and 9B depict pairwise alignments of three EBOV GP coding sequences used in the recombinant MVA-BN® based construct. The coding sequences for the GP genes originating from three EBOV strains EBOV-B, -S and -Z were aligned pairwise before (non-opt; see FIG. 9A, (SEQ ID NOs:8-10)) and after (opt; see FIG. 9B, (SEQ ID NOs:11-13)) optimization. FIG. 9A: EBOV-B non-opt SEQ ID NO: 8, EBOV-S non-opt SEQ ID NO:9, EBOV-Z non-opt SEQ ID NO:10; FIG. 9B: EBOV-B opt SEQ ID NO: 11, EBOV-S opt SEQ ID NO:12, EBOV-Z opt SEQ ID NO:13. No Gaps were allowed in the alignments. Gray background: identical nucleotide positions in the coding sequence. The identity in nucleotide positions of three genes prior (non-opt) and after (opt) optimization is tabulated in Table C.

EXAMPLES

Example 1

Preparation of Substituted, Truncated F Gene

Creation of a recombinant MVA expressing both a full-length RSV-F protein and a truncated Version RSV-F_trunc was desired. However, based on results with MVA and other vaccinia viruses containing repeat sequences, it was expected that intramolecular recombination would lead to recombination between the two copies of the F gene, resulting in deletion of one of the copies of the F gene.

To minimize the presence of long stretches of identical nucleotides between the two F genes, the codons in the nucleotide sequence encoding the RSV-F_trunc gene were substituted, while maintaining the amino acid sequence of the F genes. The use of rare codons for mammals and chickens was avoided. Also, substitutions that might introduce nucleic acid signals were avoided. Such signals included internal TATA-boxes, chi-sites, and ribosomal entry sites; AT-rich and GC-rich sequence stretches; ARE, INS, and CRS sequence elements; repeat sequences and RNA secondary structures; (cryptic) splice donor and acceptor sites, and branch points; and vaccinia termination signals (TTTTTNT). The substituted nucleotide sequence is shown in FIG. 1, compared to a coding sequence for a full-length RSV-F protein. Although significant identity remains throughout the two coding sequences, there are no remaining large stretches of identity greater than nine contiguous nucleotides within the two coding sequences. The proteins encoded by the two coding sequences are aligned in FIG. 2. The two proteins have 100% identity over the first 524 amino acids (the substituted F protein is truncated at the carboxy terminus). Thus, although these two coding nucleotide sequences encode a stretch of identical amino acids, one of the sequences has been substituted relative to the other.

Example 2

Preparation of Recombinant Viruses Comprising RSV-F Genes

The DNA encoding the full-length RSV-F gene was inserted into MVA at two different integration sites to generate MVA-mBN170B and MVA-mBN172B (in the IGR88/89 site). The substituted, RSV-F_trunc gene was inserted into MVA at the IGR148/149 site to generate MVA-mBN173B.

Figure 4A:
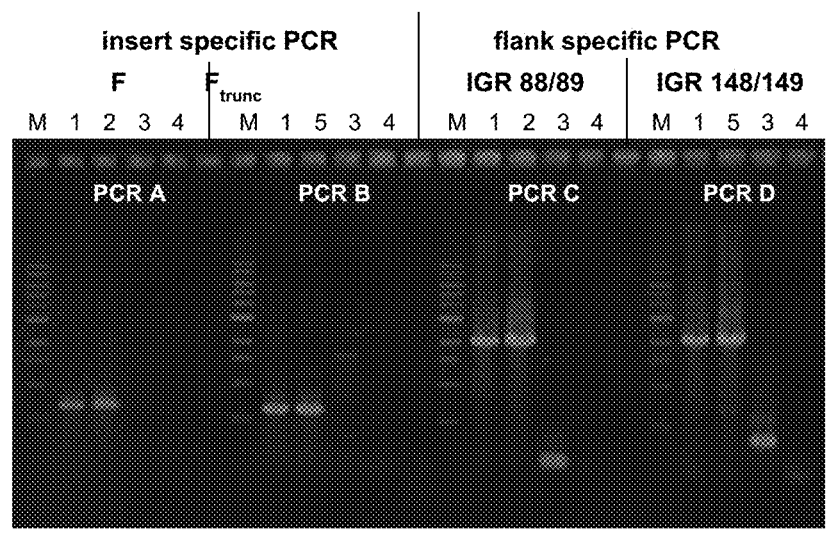
FIGS. 4A-C depict PCR analysis of MVA-mBN175B. RSV-F (F) and RSV-F_trunc (F_trunc) are shown. A. PCR results with various primer pairs. M=markers (1 kb-ladder, New England Biolabs). Lane 1 is MVA-mBN175B. Lane 2 is a positive control plasmid (pBN345). Lane 3 is MVA-mBN®. Lane 4 is a water control. Lane 5 is a positive control plasmid (pBN343). B. Schematic of MVA-mBN175B showing locations of primers used for the PCRs shown in FIG. 4A. C. Schematic of wild type MVA-mBN® showing locations of primers.
Figure 4B:
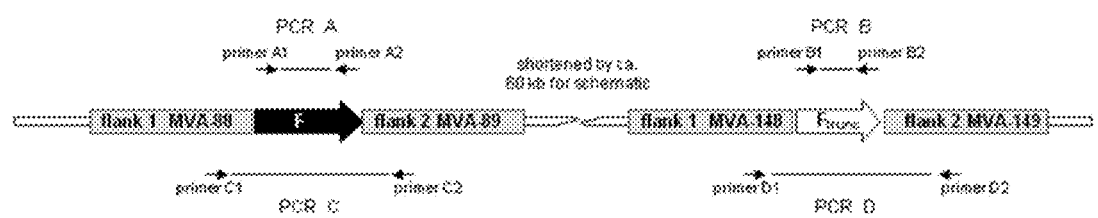
Figure 4C:
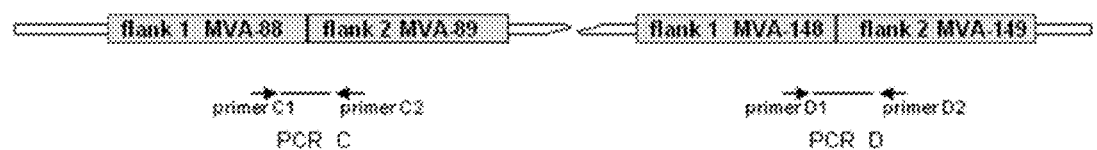

A double recombinant MVA was then created containing the full-length RSV-F gene inserted into MVA at the IGR88/89 site and the substituted, RSV-F_trunc gene inserted into the same MVA at the IGR148/149 site. The double recombinant virus was called MVA-mBN175B. A schematic of this virus is shown in FIG. 4B.

Example 3

Expression of F Proteins from Recombinant Viruses

Figure 3:
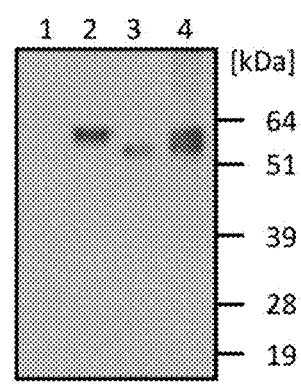
FIG. 3 depicts expression of RSV-F and RSV-F_trunc from recombinant MVA-BN® viruses in a human cell line. Western blot with extracts from infected human cells upon infection with different MVA-BN® based viruses with an MOI of 10 and lysis at 24 h post infection. MVA-BN® (empty vector control; lane 1), MVA-mBN172B (recombinant MVA-BN® with full length RSV-F; lane 2), MVA-mBN173B (recombinant MVA-BN® with truncated RSV-F_trunc; lane 3) and lane 4: MVA-mBN175B (recombinant MVA-BN® with RSV-F and RSV-F_trunc). The calculated molecular weight of the proteins is: RSV-F (61.6 kDa) and RSV-F_trunc (56.1 kDa).

To determine whether protein was expressed from the substituted nucleotide sequence, western blot analysis was performed on protein extracts from a human cell line infected with a recombinant MVA-BN®-based virus encoding the full-length RSV-F gene (MVA-mBN172B), the virus encoding the substituted, RSV-F_trunc gene (MVA-mBN173B) and a double recombinant virus encoding both, the full length and the RSV-F_trunc gene (MVA-mBN175B). All three viruses showed the production of the appropriately sized RSV-F proteins by Western blot analysis (FIG. 3), while the MVA-BN® control (empty vector) did not show any bands, as expected. Thus, the full length and the truncated F protein expressed from the substituted coding nucleotide sequence were expressed individually from single recombinant MVA-BN® but both were also co-expressed from one double recombinant MVA-BN® virus (MVA-mBN175B) in a human cell line.

Example 4

Growth of Recombinant Viruses

Chicken embryo fibroblast cells were infected with MVA-mBN175B, a construct containing both the full-length F gene and the substituted, RSV-F_trunc gene, or a construct containing only the full-length F gene to receive a first virus crude stock. Similar titers of the double recombinant virus containing both full length F and truncated F genes ($1.34 \times 10^7$ TCID50) were seen in comparison with titers of the virus containing only the full length F gene ($1.46 \times 10^7$ TCID50). These results indicated that a stable double recombinant MVA was being produced, and that recombination between the two copies of the F gene had been limited by substituting nucleotide bases in the sequences.

Example 5

PCR Analysis of Recombinant Viruses

PCR analysis was performed on DNA from cells infected with MVA-mBN175B or MVA-BN® using the insert-specific and flank-specific primer pairs depicted in FIGS. 4B and C. PCR A with primers A1/A2, which are specific for the full-length F gene, detected a band with the size of 663 base pairs (bp) in cells infected with MVA-mBN175B and in a specific plasmid positive control as expected. This band as expected is absent in cells infected with MVA-BN® or in the water control (FIG. 4A). PCR B with primers B1/B2, which are specific for the substituted, truncated F gene, detected a band with the size of 625 bp in cells infected with MVA-mBN175B and in a specific plasmid positive control as expected. This band, as expected, is absent in cells infected with MVA-BN® or in the water control (FIG. 4A). PCR C with primers C1/C2, which detect insertions into the IGR88/89 site, detected a band with the size of 2047 bp in cells infected with MVA-mBN175B and in a specific plasmid positive control as expected. This band, as expected, is absent in cells infected with the empty vector control MVA-BN®, instead a band of 161 bp indicates the wildtype situation at IGR88/89 in MVA-BN® (FIG. 4A). PCR D with primers D1/D2, which detect insertions into the IGR148/149 site, detected a band with the size of 2062 bp in cells infected with MVA-mBN175B and in a specific plasmid positive control as expected. This band as expected is absent in cells infected with the empty vector control MVA-BN®, instead a band of 360 bp indicates the wildtype situation at IGR88/89 in MVA-BN®. (FIG. 4A).

Figure 5B:
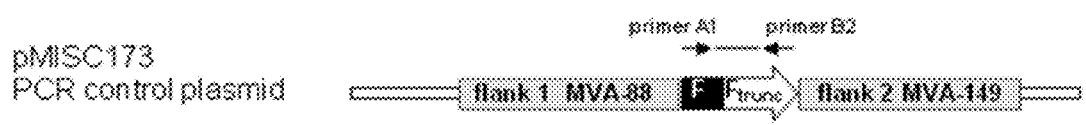
Figure 5C:
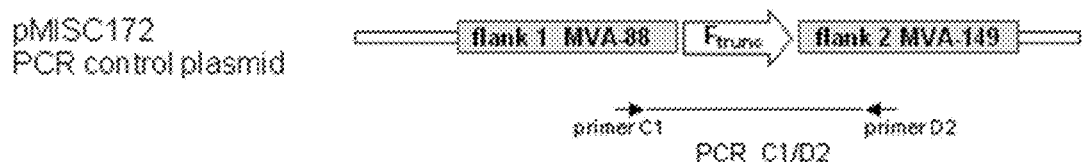
Figure 6:
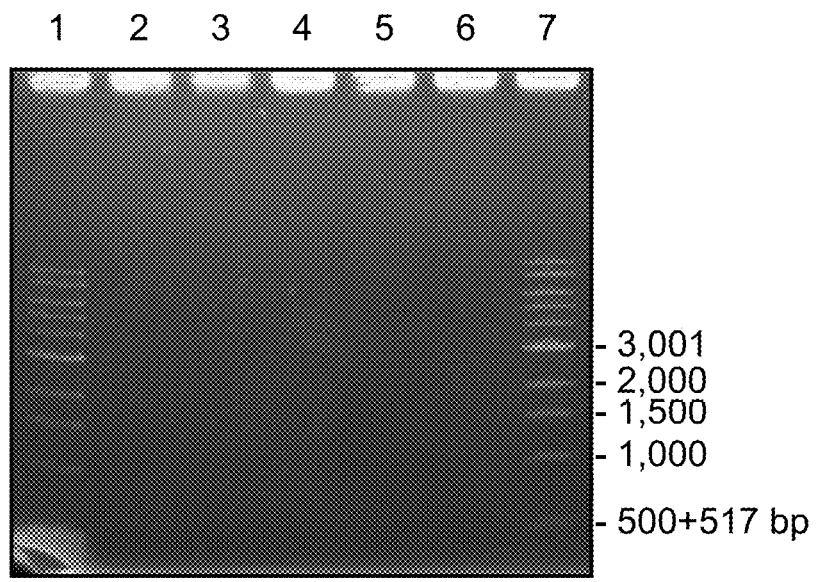
FIG. 6 depicts PCR analysis of DNA isolated from cells infected with MVA-mBN175B. Lanes 1 and 7 are marker lanes. Lane 2 is MVA-mBN175B. Lane 3 is a plasmid control for the F gene (pBN343). Lane 4 is a plasmid control for the truncated F gene (pBN345). Lane 5 is MVA-BN®. Lane 6 is a water control. The expected PCR product from a hypothetical recombination between the RSV-F gene and truncated F gene RSV-F_trunc in MVA-mBN175B is 613 base pairs.

Recombination between the F genes would yield a hybrid F gene having parts of the wild-type F gene and parts of the truncated F gene. (FIG. 5A.) To detect the presence of any such recombinants, PCR analysis was performed on DNA from cells infected with MVA-mBN175B or MVA-BN® using the primer pairs A1/B2 (FIG. 5B.), which should generate a 613 base pair product, specific for the recombinant F gene. The results of this PCR showed no detectable recombinants. (FIG. 6.) These results indicated that a stable double recombinant MVA was being produced, and that recombination between the two copies of the F gene had been limited.

Example 6

Preparation of Recombinant Glycoprotein (GP) Genes of Three Different Ebolavirus (EBOV) Strains Generation of a recombinant MVA expressing three ebolavirus (EBOV) glycoproteins (GP) was desired. The EBOV strains used herein are EBOV-B (Bundibugyo), EBOV-S (Sudan) and EBOV-Z (Zaire), all belonging to virus strains with high lethality in infected humans. Said three GP share an overall identity of 48.5%, indicating that nearly every second amino acid in the GP proteins is identical in all three strains, while the percent identities over the full-length protein sequences in comparison of combinations of two strains are between 57.0% and 64.2% (FIG. 7).

To minimize the presence of long stretches of identical nucleotides within the three EBOV GP genes, the codons in the three nucleotide sequences were substituted, while maintaining the encoded amino acid sequences of the three GP genes. The use of rare codons for mammals and chickens, as well as substitutions that might introduce nucleic acid signals were avoided. Such signals included internal TATA-boxes, chi-sites, and ribosomal entry sites; AT-rich and GC-rich sequence stretches; ARE, INS, and CRS sequence elements; repeat sequences and RNA secondary structures; (cryptic) splice donor and acceptor sites, and branch points; and vaccinia termination signals (TTTTTNT). The G after the ATG start codon allows for high expression and is present in the original coding sequence of all three EBOV GP genes and was maintained.

Although 23.3 to 24.9% of the nucleotides in each of the 3 optimized EBOV GP coding sequences were exchanged (see Table A), the overall identities did not dramatically change between the three GP coding sequences (Table B). In two cases, the pair wise comparisons even showed marginally higher identities after optimization of the coding sequences, as shown below in Table B.

TABLE A

Nucleotide exchanges in three optimized EBOV GP genes. The table shows the number of changed nucleotides at the corresponding positions in the optimized GP coding sequences (opt) compared to the non-optimized (non-opt) sequence of different EBOV strains based on the total number of nucleotides in [%]. The total number of nt is 1147.

| | exchanged nt positions in optimized GP coding sequences compared to non-optimized sequences [%] |
|---|---|
| EBOV-B non-opt: EBOV-B opt | 23.3 |
| EBOV-S non-opt: EBOV-S opt | 24.9 |
| EBOV-Z non-opt: EBOV-Z opt | 23.9 |

TABLE B

Identical nucleotide positions of three EBOV GP coding sequences. The table shows the number of identical nucleotides at the corresponding positions in two GP coding sequences of different EBOV strains based on the total number of nucleotides in [%].

| pairwise comparison of GP genes | identity of nucleotides in non-optimized genes [%] | identity of nucleotides in optimized genes [%] |
|---|---|---|
| EBOV-B: EBOV-S | 57.0 | 57.3 |
| EBOV-B: EBOV-Z | 64.2 | 61.1 |
| EBOV-S: EBOV-Z | 57.6 | 60.4 |

Pairwise alignments of the GP coding sequences of three EBOV strains EBOV-B, -S and -Z showed the identities in nucleotide positions and the distribution of identities (FIGS. 9A and 9B). Consequently, the method of the present invention led to shorter stretches of nucleotide identitity in the EBOV GP-sequences. When considering long stretches of identical consecutive nucleotides, it is evident that the interruption or shortening of such stretches of identities is an important part of the strategy to avoid recombination between sequences sharing a certain degree of nucleotide identities. In Table C (see below) the number of stretches of consecutive identical nucleotides from pair wise comparison of the GP coding sequences are shown. Prior to optimization, there are stretches of up to 23 bp length and in summary there are 41 stretches of 10 or more identical nucleotides. In the optimized version of the GP genes, only one 13 bp stretch is found and 7 stretches of 10 or more identical nucleotides can be found.

TABLE C

Long stretches of consecutive identical nucleotides. The table shows the number of stretches of consecutive identical nucleotides of a certain length in pair wise comparison of EBOV GP coding sequences before (non-opt) and after (opt) optimization. The numbers of the pairwise comparisons are summarized in the column 'combined number'. The longest stretch in the non-optimized comparisons are 23 consecutive identical nucleotides, while in the optimized genes, it is reduced to a maximum of 13 nucleotides. Only stretches of 10 or more nucleotides are listed.

| | EBOV-B: EBOV-i. S | | EBOV-B: EBOV-ii. Z | | EBOV-S: EBOV-iii. Z | | combined numbers | |
|---|---|---|---|---|---|---|---|---|
| length | non-opt | opt | non-opt | opt | non-opt | opt | non-opt | opt |
| 23 nt | | | 1 | | | | 1 | |
| 20 nt | | | 2 | | | | 2 | |
| 17 nt | | | | | 1 | | 1 | |
| 16 nt | | | 2 | | | | 2 | |
| 14 nt | | | 2 | | 2 | | 4 | |
| 13 nt | | | 1 | 1 | 1 | | 2 | 1 |
| 12 nt | 1 | | 2 | | | | 3 | |
| 11 nt | 10 | 2 | 4 | 1 | 8 | | 22 | 3 |
| 10 nt | 1 | | 2 | 1 | 1 | 2 | 4 | 3 |

Example 7

Preparation of Recombinant MVA-BN® Viruses with GP Genes of EBOV Strains.

The three EBOV GP genes were synthesized by GeneArt (Regensburg, Germany) and cloned into recombination vectors to allow for integration into MVA-BN®. A recombinant virus comprising the three optimized homologous GP gene sequences from three different EBOV strains was generated.

The transcription of the three inserted GP coding sequences is controlled by different individual early-late promoters.

Specific PCR reactions for the three optimized EBOV-GP sequences showed the presence of the three individual genes in the recombinant MVA-BN®.

Example 8

Preparation of Plasmid Comprising RSV-F Genes

Figure 10:
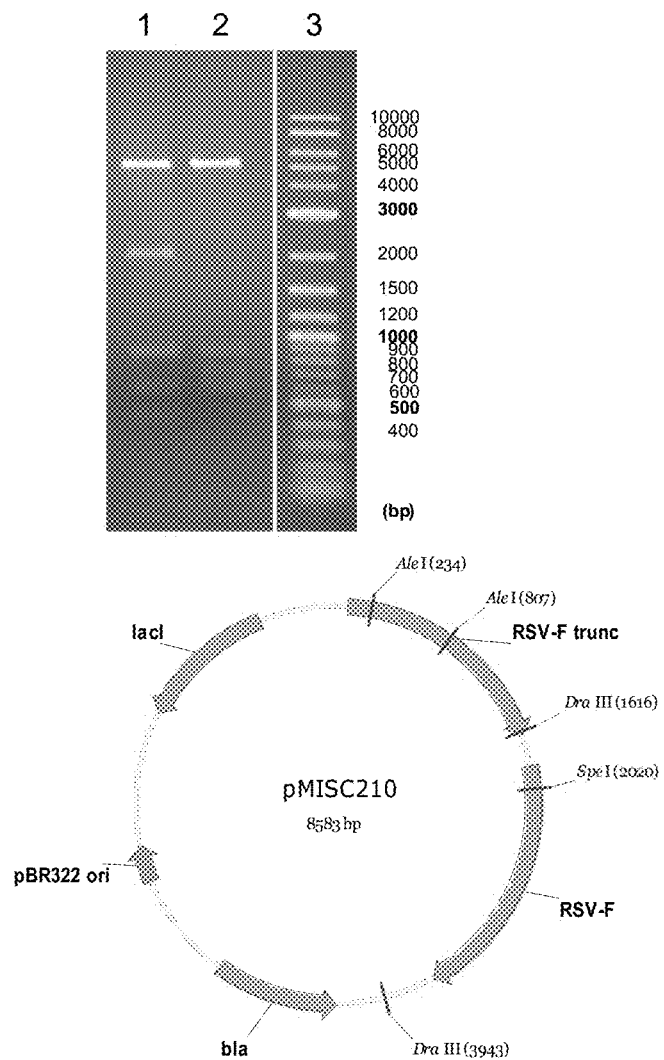
FIG. 10 depicts a restriction enzyme digest and plasmid map of plasmid pMISC210 comprising the full-length (RSV-F) and truncated (RSV-F_trunc) protein. Lane 1: plasmid pMISC210 comprising RSV-F and RSV-F_trunc; Lane 2: control plasmid pMISC209 comprising RSV-F_trunc only; Lane 3: Molecular weight marker. The size of the marker-bands in base pairs (bp) is shown.

The two versions of the RSV-F gene used in examples 1-5 and shown in FIG. 1 were cloned into one plasmid and maintained in *E. coli* TZ101 (Trenzyme GmbH, Konstanz, Germany) using standard cloning techniques. The plasmid (see plasmid map in FIG. 10) was isolated and digested with the restriction enzymes Ale I, Dra III and Spe I and separated on a 1% TAE agarose gel (see FIG. 10). The band patterns for pMISC210 encoding the full-length RSV-F protein and RSV-F_trunc protein (lane 1) as well as the control plasmid pMISC209 encoding the RSV-F_trunc protein only (lane 2) were compared with the patterns expected from the results of analysis of the electronic sequence of the plasmids. The expected size of bands for pMISC210 was 404, 573, 809, 1923 and 4874 bp, while for pMISC209 a pattern of bands with sizes of 573, 661, 809 and 4874 bp was expected. All expected bands and no additional bands were found experimentally. In case recombination between the RSV-F variants in pMISC210 occurred, one or more of the smaller fragments would be lost, depending on the sites of recombination. This was clearly not found in the current example. Thus, the results show the stability of the plasmid pMISC210 with the two RSV-F genes (RSV-F and RSV-F_trunc) in *E. coli*.

The invention claimed is:

1. A recombinant modified vaccinia Ankara (MVA) virus vector that stably encodes homologous sequences, the vector comprising:

first and second nucleotide sequences of at least 2000 nucleotides each, each nucleotide sequence encoding an Ebola virus glycoprotein;

wherein one of first and second nucleotide sequences has at least 400 substituted nucleotides and wherein the substituted nucleotides do not alter the amino acids encoded by the first and second nucleotide sequences;

wherein the first and second nucleotide sequences differ by at least 400 nucleotides; and wherein the first and second nucleotide sequences share stretches of identity of no more than 10 contiguous nucleotides; and wherein the two Ebola virus glycoprotein nucleotide sequences encode Ebola virus Sudan and Ebola virus Zaire glycoproteins.

2. The recombinant poxviral vector of claim 1, wherein the first and second nucleotide sequences encode the amino acid sequences of SEQ ID NO: 6 and SEQ ID NO: 7, respectively.

3. The recombinant poxviral vector of claim 2, wherein the first and second nucleotide sequences comprise the nucleotide sequences of SEQ ID NO: 12 and SEQ ID NO: 13, respectively.

* * * * *

SEQUENCE LISTING

```
<160> NUMBER OF SEQ ID NOS: 13

<210> SEQ ID NO 1
<211> LENGTH: 1725
<212> TYPE: DNA
<213> ORGANISM: respiratory syncytial virus

<400> SEQUENCE: 1
atggatttgc caatcctcaa aacaaatgca attaccacaa tctttgctgc agtcacactc      60
tgtttcgctt ccagtcaaaa catcactgta gaattttatc aatcaacatg cagtgcagtt     120
agcaaaggct atcttagtgc tttaagaact ggttggtata ctagtgttat aactatagaa     180
ttaagtaata tcaaggaaaa taagtgtaat ggaacagacg ctaaggtaaa attgataaaa     240
caagaattag ataaatataa aaatgctgta acagaattgc agttgctcat gcaaagcaca     300
ccagcagcca acaatcgggc cagaagagaa ctaccaaggt ttatgaatta tacactcaac     360
aataccaaaa ataacaatgt aacattaagc aagaaaagga aagaagatt tcttggcttc     420 ttgttaggtgt ttggatctgc aatcgccagt ggcattgctg tatctaaagt cctgcaccta     480 gaagggaag tgaacaaaat caaaagtgct ttactatcca caaacaaggc tgtagtcagc     540
ttatcaaatg gagttagtgt cttaaccagc aaagtgttag acctcaaaaa ctatatagat     600
aaacaattgt tacccattgt gaacaagcaa agctgcagca tatcaaacat tgaaactgtg     660
atagaattcc aacaaaagag caacagacta ctagagatta ccagggaatt tagtgttaat     720
gcaggtgtaa ctacacctgt aagcacttat atgttaacaa atagtgaatt attatcatta     780
atcaatgata tgcctataac aaatgatcag aaaaagttaa tgtccaacaa tgttcaaata     840
gttagacagc aaagttactc tatcatgtcc ataataaagg aggaagtctt agcatatgta     900
gtacaattac cactatatgg tgtaatagat acaccttgtt ggaaactaca cacatcccct     960
ctatgcacaa ccaacacaaa ggaagggtcc aacatctgtt taacaagaac cgacagagga    1020
tggtactgtg acaatgcagg atcagtgtct ttcttcccac aagctgaaac atgcaaagtt    1080
caatcgaatc gagtatttttg tgacacaatg aacagtttaa cattaccaag tgaagtaaat    1140
ctctgcaaca ttgacatatt caaccctaaa tatgattgca aaattatgac ttcaaaaaca    1200
gatgtaagca gctccgttat cacatctcta ggagccattg tgtcatgcta tggcaaaact    1260
aaatgtacag catccaataa aaatcgtgga atcataaaga catttttctaa cgggtgtgat    1320 tatgtatcaa acaagggggt ggacactgta tctgtaggta atacgttata ttatgtaaat    1380
aagcaagaag gaaaagtct ctatgtaaaa ggtgaaccaa taataaattt ctatgaccca    1440
```

```
ttagtgttcc cttctgatga atttgatgca tcaatatctc aagtcaatga gaagattaac    1500
cagagcctag catttattcg taaatccgat gaattattac ataatgtaaa tgttggtaaa    1560
tccaccacaa atatcatgat aactactata attatagtga ttatagtaat attgttatta    1620
ttaattgcag ttgggctgtt cctatactgc aaggccagaa gcacaccagt cacactaagc    1680
aaggatcaac tgagtggtat aaataatatt gcatttagta actga                   1725

<210> SEQ ID NO 2
<211> LENGTH: 1575
<212> TYPE: DNA
<213> ORGANISM: respiratory syncytial virus

<400> SEQUENCE: 2
atggatctcc ccattctcaa gaccaacgcc atcaccacca tcttcgccgc cgtgaccctg      60
tgtttcgcca gcagccagaa catcaccgtg gagttctacc agagcacctg cagcgccgtg     120
agcaagggct acctgagcgc cctgaggacc ggctggtaca ccagcgtgat caccatcgag     180
ctgtccaaca tcaaagaaaa caagtgcaac ggcaccgacg ccaaagtgaa gctgatcaag     240
caggaactgg acaagtacaa gaacgccgtg accgagctgc agctgctgat gcagagcacc     300
cctgccgcca caacagagc caggcgcgag ctgccccggt tcatgaacta caccctgaac     360
aacaccaaga caacaacgt gaccctgagc aagaagcgga agcggcggtt cctgggcttt     420
ctgctgggcg tgggcagcgc cattgccagc ggcattgccg tgtctaaggt cctgcatctg     480
gaaggcgagg tcaacaagat taagagcgcc ctgctgtcca ccaacaaggc cgtggtgtcc     540
ctgagcaacg gcgtgagcgt gctgaccagc aaggtgctgg atctgaagaa ctacatcgac     600
aagcagctgc tgcccatcgt gaataagcag tcctgcagca tcagcaacat cgagacagtg     660
atcgagttcc agcagaagag caaccggctg ctggaaatca cccgggagtt cagcgtgaat     720
gccggcgtga ccaccccccgt gtccacctac atgctgacca cagcgagct gctgtccctg     780 atcaatgaca tgcccatcac caacgaccaa aagaaactga tgagcaacaa cgtgcagatc     840
gtgcggcagc agagctacag catcatgagc atcatcaaag aagaggtgct ggcctacgtg     900
gtgcagctgc cctgtacgg cgtgatcgac accccctgct ggaagctgca caccagcccc     960
ctgtgcacca ccaacaccaa agagggcagc aacatctgcc tgacccggac cgatagggc    1020 tggtactgcg acaacgccgg cagcgtgtcc ttctttcccc aagccgagac ttgcaaggtg    1080
cagagcaaca gggtgttctg cgacaccatg aacagcctga cctgcccag cgaagtgaac    1140 ctgtgcaaca tcgacatctt taaccccaag tacgactgca agatcatgac ctccaagacc    1200
gacgtgtcca gctccgtgat taccagcctg ggcgccatcg tgtcctgcta cggcaagacc    1260
aagtgcaccg ccagcaacaa gaaccggggc atcatcaaga ccttcagcaa cggctgcgac    1320
tacgtgtcca ataagggcgt ggacaccgtg tccgtgggca acacactgta ctacgtgaac    1380
aagcaggaag gcaagagcct gtacgtgaag ggcgagccca tcatcaactt ctacgacccc    1440
ctggtgttcc ccagcgacga gttcgacgcc agcatcagcc aagtgaacga gaagatcaat    1500
cagtccctgg ccttcatcag gaagagcgac gagctgctgc acaatgtgaa cgtgggcaag    1560
tccaccacca actga                                                    1575

<210> SEQ ID NO 3
<211> LENGTH: 574
<212> TYPE: PRT
<213> ORGANISM: respiratory syncytial virus

<400> SEQUENCE: 3
```

```
Met Asp Leu Pro Ile Leu Lys Thr Asn Ala Ile Thr Ile Phe Ala
1               5                   10                  15

Ala Val Thr Leu Cys Phe Ala Ser Ser Gln Asn Ile Thr Val Glu Phe
            20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
50                      55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
                100                 105                 110

Arg Phe Met Asn Tyr Thr Leu Asn Asn Thr Lys Asn Asn Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
210                 215                 220

Gln Lys Ser Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Ile
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415
```

-continued

```
Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Val Gly Lys Ser Thr Thr Asn Ile Met Ile Thr
        515                 520                 525

Thr Ile Ile Ile Val Ile Ile Val Ile Leu Leu Leu Ile Ala Val
    530                 535                 540

Gly Leu Phe Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570
```

<210> SEQ ID NO 4
<211> LENGTH: 524
<212> TYPE: PRT
<213> ORGANISM: respiratory syncytial virus

<400> SEQUENCE: 4

```
Met Asp Leu Pro Ile Leu Lys Thr Asn Ala Ile Thr Thr Ile Phe Ala
1               5                   10                  15

Ala Val Thr Leu Cys Phe Ala Ser Ser Gln Asn Ile Thr Val Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Thr Lys Asn Asn Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220
```

```
Gln Lys Ser Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Le

```
                65                  70                  75                  80
        Thr Ala Thr Lys Arg Trp Gly Phe Arg Ala Gly Val Pro Pro Lys Val
                            85                  90                  95

Val Asn Tyr Glu Ala Gly Glu Trp Ala Glu Asn Cys Tyr Asn Leu Asp
                            100                 105                 110

Ile Lys Lys Ala Asp Gly Ser Glu Cys Leu Pro Glu Ala Pro Glu Gly
                            115                 120                 125

Val Arg Gly Phe Pro Arg Cys Arg Tyr Val His Lys Val Ser Gly Thr
                    130                 135                 140

Gly Pro Cys Pro Glu Gly Tyr Ala Phe His Lys Glu Gly Ala Phe Phe
        145                 150                 155                 160

Leu Tyr Asp Arg Leu Ala Ser Thr Ile Ile Tyr Arg Ser Thr Thr Phe
                            165                 170                 175

Ser Glu Gly Val Val Ala Phe Leu Ile Leu Pro Glu Thr Lys Lys Asp
                    180                 185                 190

Phe Phe Gln Ser Pro Pro Leu His Glu Pro Ala Asn Met Thr Thr Asp
                    195                 200                 205

Pro Ser Ser Tyr Tyr His Thr Val Thr Leu Asn Tyr Val Ala Asp Asn
        210                 215                 220

Phe Gly Thr Asn Met Thr Asn Phe Leu Phe Gln Val Asp His Leu Thr
        225                 230                 235                 240

Tyr Val Gln Leu Glu Pro Arg Phe Thr Pro Gln Phe Leu Val Gln Leu
                            245                 250                 255

Asn Glu Thr Ile Tyr Thr Asn Gly Arg Arg Ser Asn Thr Thr Gly Thr
                    260                 265                 270

Leu Ile Trp Lys Val Asn Pro Thr Val Asp Thr Gly Val Gly Glu Trp
                    275                 280                 285

Ala Phe Trp Glu Asn Lys Lys Asn Phe Thr Lys Thr Leu Ser Ser Glu
                    290                 295                 300

Glu Leu Ser Val Ile Phe Val Pro Arg Ala Gln Asp Pro Gly Ser Asn
        305                 310                 315                 320

Gln Lys Thr Lys Val Thr Pro Thr Ser Phe Ala Asn Asn Gln Thr Ser
                            325                 330                 335

Lys Asn His Glu Asp Leu Val Pro Glu Asp Pro Ala Ser Val Val Gln
                    340                 345                 350

Val Arg Asp Leu Gln Arg Glu Asn Thr Val Pro Thr Pro Pro Pro Asp
                    355                 360                 365

Thr Val Pro Thr Thr Leu Ile Pro Asp Thr Met Glu Glu Gln Thr Thr
                    370                 375                 380

Ser His Tyr Glu Pro Pro Asn Ile Ser Arg Asn His Gln Glu Arg Asn
        385                 390                 395                 400

Asn Thr Ala His Pro Glu Thr Leu Ala Asn Asn Pro Pro Asp Asn Thr
                            405                 410                 415

Thr Pro Ser Thr Pro Pro Gln Asp Gly Glu Arg Thr Ser Ser His Thr
                    420                 425                 430

Thr Pro Ser Pro Arg Pro Val Pro Thr Ser Thr Ile His Pro Thr Thr
                    435                 440                 445

Arg Glu Thr His Ile Pro Thr Thr Met Thr Thr Ser His Asp Thr Asp
                    450                 455                 460

Ser Asn Arg Pro Asn Pro Ile Asp Ile Ser Glu Ser Thr Glu Pro Gly
        465                 470                 475                 480

Pro Leu Thr Asn Thr Thr Arg Gly Ala Ala Asn Leu Leu Thr Gly Ser
                    485                 490                 495
```

```
Arg Arg Thr Arg Arg Glu Ile Thr Leu Arg Thr Gln Ala Lys Cys Asn
            500                 505                 510
Pro Asn Leu His Tyr Trp Thr Thr Gln Asp Glu Gly Ala Ala Ile Gly
            515                 520                 525
Leu Ala Trp Ile Pro Tyr Phe Gly Pro Ala Ala Glu Gly Ile Tyr Thr
            530                 535                 540
Glu Gly Ile Met His Asn Gln Asn Gly Leu Ile Cys Gly Leu Arg Gln
545                 550                 555                 560
Leu Ala Asn Glu Thr Thr Gln Ala Leu Gln Leu Phe Leu Arg Ala Thr
                565                 570                 575
Thr Glu Leu Arg Thr Phe Ser Ile Leu Asn Arg Lys Ala Ile Asp Phe
            580                 585                 590
Leu Leu Gln Arg Trp Gly Gly Thr Cys His Ile Leu Gly Pro Asp Cys
            595                 600                 605
Cys Ile Glu Pro His Asp Trp Thr Lys Asn Ile Thr Asp Lys Ile Asp
            610                 615                 620
Gln Ile Ile His Asp Phe Ile Asp Lys Pro Leu Pro Asp Gln Thr Asp
625                 630                 635                 640
Asn Asp Asn Trp Trp Thr Gly Trp Arg Gln Trp Val Pro Ala Gly Ile
                645                 650                 655
Gly Ile Thr Gly Val Ile Ile Ala Val Ile Ala Leu Leu Cys Ile Cys
            660                 665                 670
Lys Phe Leu Leu
            675

<210> SEQ ID NO 6
<211> LENGTH: 676
<212> TYPE: PRT
<213> ORGANISM: Sudan ebolavirus strain Gulu

<400> SEQUENCE: 6

Met Gly Gly Leu Ser Leu Leu Gln Leu Pro Arg Asp Lys Phe Arg Lys
1               5                   10                  15
Ser Ser Phe Phe Val Trp Val Ile Ile Leu Phe Gln Lys Ala Phe Ser
            20                  25                  30
Met Pro Leu Gly Val Val Thr Asn Ser Thr Leu Glu Val Thr Glu Ile
            35                  40                  45
Asp Gln Leu Val Cys Lys Asp His Leu Ala Ser Thr Asp Gln Leu Lys
            50                  55                  60
Ser Val Gly Leu Asn Leu Glu Gly Ser Gly Val Ser Thr Asp Ile Pro
65              70                  75                  80
Ser Ala Thr Lys Arg Trp Gly Phe Arg Ser Gly Val Pro Pro Lys Val
                85                  90                  95
Val Ser Tyr Glu Ala Gly Glu Trp Ala Glu Asn Cys Tyr Asn Leu Glu
            100                 105                 110
Ile Lys Lys Pro Asp Gly Ser Glu Cys Leu Pro Pro Pro Pro Asp Gly
            115                 120                 125
Val Arg Gly Phe Pro Arg Cys Arg Tyr Val His Lys Ala Gln Gly Thr
            130                 135                 140
Gly Pro Cys Pro Gly Asp Tyr Ala Phe His Lys Asp Gly Ala Phe Phe
145                 150                 155                 160
Leu Tyr Asp Arg Leu Ala Ser Thr Val Ile Tyr Arg Gly Val Asn Phe
                165                 170                 175
Ala Glu Gly Val Ile Ala Phe Leu Ile Leu Ala Lys Pro Lys Glu Thr
```

```
            180                 185                 190
Phe Leu Gln Ser Pro Pro Ile Arg Glu Ala Val Asn Tyr Thr Glu Asn
            195                 200                 205
Thr Ser Ser Tyr Tyr Ala Thr Ser Tyr Leu Glu Tyr Glu Ile Glu Asn
            210                 215                 220
Phe Gly Ala Gln His Ser Thr Thr Leu Phe Lys Ile Asp Asn Asn Thr
225                 230                 235                 240
Phe Val Arg Leu Asp Arg Pro His Thr Pro Gln Phe Leu Phe Gln Leu
                245                 250                 255
Asn Asp Thr Ile His Leu His Gln Gln Leu Ser Asn Thr Thr Gly Arg
                260                 265                 270
Leu Ile Trp Thr Leu Asp Ala Asn Ile Asn Ala Asp Ile Gly Glu Trp
                275                 280                 285
Ala Phe Trp Glu Asn Lys Lys Asn Leu Ser Glu Gln Leu Arg Gly Glu
                290                 295                 300
Glu Leu Ser Phe Glu Ala Leu Ser Leu Asn Glu Thr Glu Asp Asp Asp
305                 310                 315                 320
Ala Ala Ser Ser Arg Ile Thr Lys Gly Arg Ile Ser Asp Arg Ala Thr
                325                 330                 335
Arg Lys Tyr Ser Asp Leu Val Pro Lys Asn Ser Pro Gly Met Val Pro
                340                 345                 350
Leu His Ile Pro Glu Gly Glu Thr Thr Leu Pro Ser Gln Asn Ser Thr
                355                 360                 365
Glu Gly Arg Arg Val Gly Val Asn Thr Gln Glu Thr Ile Thr Glu Thr
                370                 375                 380
Ala Ala Thr Ile Ile Gly Thr Asn Gly Asn His Met Gln Ile Ser Thr
385                 390                 395                 400
Ile Gly Ile Arg Pro Ser Ser Ser Gln Ile Pro Ser Ser Ser Pro Thr
                405                 410                 415
Thr Ala Pro Ser Pro Glu Ala Gln Thr Pro Thr Thr His Thr Ser Gly
                420                 425                 430
Pro Ser Val Met Ala Thr Glu Glu Pro Thr Thr Pro Gly Ser Ser
                435                 440                 445
Pro Gly Pro Thr Thr Glu Ala Pro Thr Leu Thr Thr Pro Glu Asn Ile
                450                 455                 460
Thr Thr Ala Val Lys Thr Val Leu Pro Gln Glu Ser Thr Ser Asn Gly
465                 470                 475                 480
Leu Ile Thr Ser Thr Val Thr Gly Ile Leu Gly Ser Leu Gly Leu Arg
                485                 490                 495
Lys Arg Ser Arg Arg Gln Thr Asn Thr Lys Ala Thr Gly Lys Cys Asn
                500                 505                 510
Pro Asn Leu His Tyr Trp Thr Ala Gln Glu Gln His Asn Ala Ala Gly
                515                 520                 525
Ile Ala Trp Ile Pro Tyr Phe Gly Pro Gly Ala Glu Gly Ile Tyr Thr
                530                 535                 540
Glu Gly Leu Met His Asn Gln Asn Ala Leu Val Cys Gly Leu Arg Gln
545                 550                 555                 560
Leu Ala Asn Glu Thr Thr Gln Ala Leu Gln Leu Phe Leu Arg Ala Thr
                565                 570                 575
Thr Glu Leu Arg Thr Tyr Thr Ile Leu Asn Arg Lys Ala Ile Asp Phe
                580                 585                 590
Leu Leu Arg Arg Trp Gly Gly Thr Cys Arg Ile Leu Gly Pro Asp Cys
                595                 600                 605
```

```
Cys Ile Glu Pro His Asp Trp Thr Lys Asn Ile Thr Asp Lys Ile Asn
            610                 615                 620

Gln Ile Ile His Asp Phe Ile Asp Asn Pro Leu Pro Asn Gln Asp Asn
625                 630                 635                 640

Asp Asp Asn Trp Trp Thr Gly Trp Arg Gln Trp Ile Pro Ala Gly Ile
                645                 650                 655

Gly Ile Thr Gly Ile Ile Ile Ala Ile Ile Ala Leu Leu Cys Val Cys
                660                 665                 670

Lys Leu Leu Cys
            675

<210> SEQ ID NO 7
<211> LENGTH: 676
<212> TYPE: PRT
<213> ORGANISM: Zaire ebolavirus Mayinga strain

<400> SEQUENCE: 7

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
                20                  25                  30

Ile Pro Leu Gly Val Ile His Asn Ser Thr Leu Gln Val Ser Asp Val
            35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Asn Leu Thr Arg Lys Ile Arg Ser Glu
```

```
            290                 295                 300
Glu Leu Ser Phe Thr Val Val Ser Asn Gly Ala Lys Asn Ile Ser Gly
305                 310                 315                 320

Gln Ser Pro Ala Arg Thr Ser Ser Asp Pro Gly Thr Asn Thr Thr Thr
            325                 330                 335

Glu Asp His Lys Ile Met Ala Ser Glu Asn Ser Ser Ala Met Val Gln
        340                 345                 350

Val His Ser Gln Gly Arg Glu Ala Ala Val Ser His Leu Thr Thr Leu
    355                 360                 365

Ala Thr Ile Ser Thr Ser Pro Gln Ser Leu Thr Thr Lys Pro Gly Pro
370                 375                 380

Asp Asn Ser Thr His Asn Thr Pro Val Tyr Lys Leu Asp Ile Ser Glu
385                 390                 395                 400

Ala Thr Gln Val Glu Gln His His Arg Arg Thr Asp Asn Asp Ser Thr
            405                 410                 415

Ala Ser Asp Thr Pro Ser Ala Thr Thr Ala Ala Gly Pro Pro Lys Ala
        420                 425                 430

Glu Asn Thr Asn Thr Ser Lys Ser Thr Asp Phe Leu Asp Pro Ala Thr
    435                 440                 445

Thr Thr Ser Pro Gln Asn His Ser Glu Thr Ala Gly Asn Asn Asn Thr
450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
            485                 490                 495

Arg Arg Thr Arg Arg Glu Ala Ile Val Asn Ala Gln Pro Lys Cys Asn
        500                 505                 510

Pro Asn Leu His Tyr Trp Thr Thr Gln Asp Glu Gly Ala Ala Ile Gly
    515                 520                 525

Leu Ala Trp Ile Pro Tyr Phe Gly Pro Ala Ala Glu Gly Ile Tyr Ile
530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
            565                 570                 575

Thr Glu Leu Arg Thr Phe Ser Ile Leu Asn Arg Lys Ala Ile Asp Phe
        580                 585                 590

Leu Leu Gln Arg Trp Gly Gly Thr Cys His Ile Leu Gly Pro Asp Cys
    595                 600                 605

Cys Ile Glu Pro His Asp Trp Thr Lys Asn Ile Thr Asp Lys Ile Asp
610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
            645                 650                 655

Gly Val Thr Gly Val Ile Ile Ala Val Ile Ala Leu Phe Cys Ile Cys
        660                 665                 670

Lys Phe Val Phe
    675

<210> SEQ ID NO 8
<211> LENGTH: 2031
<212> TYPE: DNA
<213> ORGANISM: Ebolavirus bundibugyo
```

<400> SEQUENCE: 8

```
atggttacat caggaattct acaattgccc cgtgaacgct tcagaaaaac atcattttt     60
gtttgggtaa taatcctatt tcacaaagtt ttccctatcc cattgggcgt agttcacaac    120
aacactctcc aggtaagtga tatagataaa ttggtgtgcc gggataaact ttcctccaca    180
agtcagctga aatcggtcgg gcttaatcta gaaggtaatg gagttgccac agatgtacca    240
acagcaacga agagatgggg attccgagct ggtgttccac ccaaagtggt gaactacgaa    300
gctggggagt gggctgaaaa ctgctacaac ctggacatca agaaagcaga tggtagcgaa    360
tgcctacctg aagcccctga gggtgtaaga ggcttccctc gctgccgtta tgtgcacaag    420
gtttctggaa cagggccgtg ccctgaaggt tacgctttcc acaagaagg cgctttcttc     480
ctgtatgatc gactggcatc aacaatcatc tatcgaagca ccacgttttc agaaggtgtt    540
gtggctttct tgatcctccc cgaaactaaa aaggactttt tccaatcgcc accactacat    600
gaaccggcca atatgacaac agacccatcc agctactacc acacagtcac acttaattat    660
gtggctgaca attttgggac caatatgact aactttctgt ttcaagtgga tcatctaact    720
tatgtgcaac ttgaaccaag attcacacca caatttcttg tccaactcaa tgagaccatt    780
tatactaatg gcgtcgcag caacaccaca ggaacactaa tttggaaagt aaatcctact     840
gttgacaccg cgtaggtga atgggccttc tgggaaaata agaagaactt cacaaaaacc    900
ctttcaagtg aagagctgtc tgtcatattt gtaccaagag cccaggatcc aggcagcaac    960
cagaagacga aggtcactcc caccagcttc gccaacaacc aaacctccaa gaaccacgaa   1020
gacttggttc cagaggatcc cgcttcagtg gttcaagtgc gagacctcca gagggaaaac   1080
acagtgccga ccccaccccc agacacagtc cccacaactc tgatcccga cacaatggag    1140
gaacaaacca ccagccacta cgaaccacca aacatttcca gaaaccatca agagaggaac   1200
aacaccgcac accccgaaac tctcgccaac aatccccag acaacacaac cccgtcgaca    1260
ccacctcaag acggtgagcg gacaagttcc cacacaacac cctcccccg cccagtccca    1320
accagcacaa tccatcccac cacacgagag actcacattc ccaccacaat gacaacaagc    1380
catgacaccg acagcaatcg acccaaccca attgacatca gcgagtctac agagccagga   1440
ccactcacca acaccacaag aggggctgca atctgctga caggctcaag aagaacccga    1500
agggaaatca ccctgagaac acaagccaaa tgcaacccaa acctacacta ttggacaacc   1560
caagatgaag gggctgccat tggtttagcc tggatacctt acttcgggcc cgcagcagag   1620
ggaatttata cggaagggat aatgcacaat caaaatgggc taatttgcgg gttgaggcag   1680
ctagcaaatg agacgactca agccctacag ttattcttgc gtgctaccac ggaattgcgc    1740
actttctcta tattgaatcg aaaagccatc gacttttac tccaaagatg gggaggaacg     1800
tgccacatct taggcccaga ttgctgtatt gagccccatg attggactaa gaacattact    1860
gacaaaatag atcaaatcat tcatgatttc attgataaac ctctaccaga tcaaacagat   1920
aatgacaatt ggtggacagg gtggaggcaa tgggttcctg ccgggatcgg gatcacgggg   1980
gtaataatcg cagttatagc actgctgtgt atttgcaaat ttctactcta a            2031
```

<210> SEQ ID NO 9
<211> LENGTH: 2031
<212> TYPE: DNA
<213> ORGANISM: Sudan ebolavirus strain Gulu

<400> SEQUENCE: 9

| | |
|---|---:|
| atgggggtc ttagcctact ccaattgccc agggacaaat ttcggaaaag ctctttctttt | 60 |
| gtttgggtca tcatcttatt ccaaaaggcc ttttccatgc ctttgggtgt tgtgactaac | 120 |
| agcactttag aagtaacaga gattgaccag ctagtctgca aggatcatct tgcatctact | 180 |
| gaccagctga aatcagttgg tctcaacctc gaggggagcg gagtatctac tgatatccca | 240 |
| tctgcaacaa agcgttgggg cttcagatct ggtgttcctc ccaaggtggt cagctatgaa | 300 |
| gcggagaat gggctgaaaa ttgctacaat cttgaaataa agaagccgga cgggagcgaa | 360 |
| tgcttacccc caccgccaga tggtgtcaga ggctttccaa ggtgccgcta tgttcacaaa | 420 |
| gcccaaggaa ccgggccctg cccaggtgac tacgcctttc acaaggatgg agctttcttc | 480 |
| ctctatgaca ggctggcttc aactgtaatt tacagaggag tcaattttgc tgaggggta | 540 |
| attgcattct tgatattggc taaaccaaaa gaaacgttcc ttcagtcacc ccccattcga | 600 |
| gaggcagtaa actacactga aaatacatca agttattatg ccacatccta cttggagtat | 660 |
| gaaatcgaaa attttggtgc tcaacactcc acgaccctt tcaaaattga caataatact | 720 |
| tttgttcgtc tggacaggcc ccacacgcct cagttccttt tccagctgaa tgataccatt | 780 |
| caccttcacc aacagttgag taatacaact gggagactaa tttggacact agatgctaat | 840 |
| atcaatgctg atattggtga atgggctttt tgggaaaata aaaaaaatct ctccgaacaa | 900 |
| ctacgtggag aagagctgtc tttcgaagct ttatcgctca cgagacaga gacgatgat | 960 |
| gcggcatcgt cgagaattac aaagggaaga atctccgacc gggccaccag gaagtattcg | 1020 |
| gacctggttc aaagaattc ccctgggatg gttccattgc ataccaga aggggaaaca | 1080 |
| acattgccgt ctcagaattc gacagaaggt cgaagagtag tgtgtaacac tcaggagacc | 1140 |
| attacagaga cagctgcaac aattataggc actaacggca accatatgca gatctccacc | 1200 |
| atcgggataa gaccgagctc cagccaaatc ccgagttcct caccgaccac ggcaccaagc | 1260 |
| cctgaggctc agaccccac aacccacaca tcaggtccat cagtgatggc caccgaggaa | 1320 |
| ccaacaacac caccgggaag ctcccccggc ccaacaacag aagcacccac tctcaccacc | 1380 |
| ccagaaaata taacaacagc ggttaaaact gtcctgccac aggagtccac aagcaacggt | 1440 |
| ctaataactt caacagtaac agggattctt gggagtcttg gcttcgaaa acgcagcaga | 1500 |
| agacaaacta acaccaaagc cacgggtaag tgcaatccca acttacacta ctggactgca | 1560 |
| caagaacaac ataatgctgc tgggattgcc tggatcccgt actttggacc gggtgcggaa | 1620 |
| ggcatataca ctgaaggcct gatgcataac caaaatgcct tagtctgtgg acttaggcaa | 1680 |
| cttgcaaatg aaacaactca agctctgcag cttttcttaa gagccacaac ggagctgcgg | 1740 |
| acatatacca tactcaatag gaaggccata gatttccttc tgcgacgatg gggcgggaca | 1800 |
| tgcaggatcc tgggaccaga ttgttgcatt gagccacatg attggacaaa aacatcact | 1860 |
| gataaaatca accaaatcat ccatgatttc atcgacaacc ccttacctaa tcaggataat | 1920 |
| gatgataatt ggtggacggg ctggagacag tggatccctg caggaataggcattactgga | 1980 |
| attattattg caattattgc tcttctttgc gtttgcaagc tgctttgctg a | 2031 |

<210> SEQ ID NO 10
<211> LENGTH: 2031
<212> TYPE: DNA
<213> ORGANISM: Zaire ebolavirus Mayinga strain

<400> SEQUENCE: 10

| | |
|---|---:|
| atgggcgtta caggaatatt gcagttacct cgtgatcgat tcaagaggac atcattctt | 60 |
| ctttgggtaa ttatccttttt ccaaagaaca ttttccatcc cacttggagt catccacaat | 120 |

```
agcacattac aggttagtga tgtcgacaaa ctagtttgtc gtgacaaact gtcatccaca    180
aatcaattga gatcagttgg actgaatctc aagggaatg gagtggcaac tgacgtgcca    240
tctgcaacta aaagatgggg cttcaggtcc ggtgtcccac caaggtggt caattatgaa    300 gctggtgaat gggctgaaaa ctgctacaat cttgaaatca aaaaacctga cgggagtgag    360
tgtctaccag cagcgccaga cgggattcgg ggcttccccc ggtgccggta tgtgcacaaa    420
gtatcaggaa cgggaccgtg tgccggagac tttgccttcc ataaagaggg tgctttcttc    480
ctgtatgatc gacttgcttc cacagttatc taccgaggaa cgactttcgc tgaaggtgtc    540
gttgcatttc tgatactgcc ccaagctaag aaggacttct tcagctcaca ccccttgaga    600
gagccggtca tgcaacggga ggacccgtct agtggctact attctaccac aattagatat    660
caggctaccg gttttggaac caatgagaca gagtacttgt tcgaggttga caatttgacc    720
tacgtccaac ttgaatcaag attcacacca cagtttctgc tccagctgaa tgagacaata    780
tatacaagtg ggaaaaggag caataccacg ggaaaactaa tttggaaggt caaccccgaa    840
attgatacaa caatcgggga gtgggccttc tgggaaacta aaaaaaaacct cactagaaaa    900 attcgcagtg aagagttgtc tttcacagtt gtatcaaacg gagccaaaaa catcagtggt    960
cagagtccgg cgcgaacttc ttccgaccca gggaccaaca caacaactga agaccacaaa   1020
atcatggctt cagaaaattc ctctgcaatg gttcaagtgc acagtcaagg aagggaagct   1080
gcagtgtcgc atctaacaac ccttgccaca atctccacga gtccccaatc cctcacaacc   1140
aaaccaggtc cggacaacag cacccataat acacccgtgt ataaacttga catctctgag   1200
gcaactcaag ttgaacaaca tcaccgcaga acagacaacg acagcacagc ctccgacact   1260
ccctctgcca cgaccgcagc cggacccca aaagcagaga acaccaacac gagcaagagc   1320
actgacttcc tggaccccgc caccacaaca agtccccaaa accacagcga accgctggc    1380 aacaacaaca ctcatcacca agataccgga gaagagagtg ccagcagcgg gaagctaggc   1440
ttaattacca atactattgc tggagtcgca ggactgatca caggcgggag aagaactcga   1500
agagaagcaa ttgtcaatgc tcaacccaaa tgcaacccta atttacatta ctggactact   1560
caggatgaag gtgctgcaat cggactggcc tggataccat atttcgggcc agcagccgag   1620
ggaatttaca tagaggggct aatgcacaat caagatggtt taatctgtgg gttgagacag   1680
ctggccaacg agacgactca agctcttcaa ctgttcctga gagccacaac tgagctacgc   1740
accttttcaa tcctcaaccg taaggcaatt gatttcttgc tgcagcgatg gggcggcaca   1800
tgccacattc tgggaccgga ctgctgtatc gaaccacatg attggaccaa gaacataaca   1860
gacaaaattg atcagattat tcatgatttt gttgataaaa cccttccgga ccaggggac    1920 aatgacaatt ggtggacagg atggagacaa tggatccgg caggtattgg agttacaggc   1980
gttataattg cagttatcgc tttattctgt atatgcaaat ttgtcttta g              2031
```

<210> SEQ ID NO 11
<211> LENGTH: 2031
<212> TYPE: DNA
<213> ORGANISM: Ebolavirus bundibugyo

<400> SEQUENCE: 11

```
atggtcacat ctggaattct ccagctccct agggaacggt tccggaaaac cagtttcttt     60
gtctgggtca tcatcctctt ccataaggtg ttccctatcc ccctgggggt cgtccataac    120
aatacattgc aagtgtcaga tatcgataag ttggtgtgtc gcgataaact gtcatctacc    180
```

```
tctcagctga aaagcgtcgg cctcaacctc gaagggaatg gtgtcgccac tgatgtccct      240
actgccacaa aacgatgggg tttccgggct ggtgtcccccc caaaagtggt caactatgaa     300
gctggcgaat gggcagagaa ttgctataat ctggacatta aaaaggccga tggctccgag     360
tgtctccctg aagctcctga gggcgtgcgg ggattcccaa gatgtcgcta cgtccataaa     420
gtgtctggca ccggcccttg ccctgaagga tacgcctttc ataaagaagg ggcctttttc     480
ctctatgatc gcctggcttc cacaattatc tatcgctcta ctacctttc cgaggggtg       540
gtcgcttttc tcatcctccc cgagacaaag aaagatttct ttcagagtcc cccctgcat    600
gagcctgcca atatgactac cgatccttcc tcttactatc ataccgtgac actcaattat     660
gtcgctgata acttcggcac taacatgacc aactttctgt tccaggtcga ccacctgaca     720
tatgtccagc tcgagcctcg ctttacccca cagttcctgg tccagctcaa tgaaactatc     780
tatactaacg gacggcgctc taataccacc gggacccctca tttggaaagt caatcccact    840
gtcgataccg gcgtcggaga gtgggccttt tgggaaaaca agaagaactt taccaagacc    900
ctgagtagcg aggaactctc tgtgatcttt gtgcctcgcg ctcaggatcc tggatccaac     960
cagaaaccca agtgacacc tacatctttt gccaacaacc agacaagcaa gaaccatgag   1020
gacctcgtcc ccgaagatcc tgcctctgtg gtccaggtcc gggacctcca gcgcgaaaat   1080
accgtgccta ctccccccccc tgataccgtc cctactaccc tcattcccga tacaatggaa   1140
gaacagacca cctctcatta cgagccacct aacatctcca gaaatcacca ggaacgaaat   1200
aacaccgctc atcccgagac tctggctaat aacccccccg acaatactac ccctagtacc   1260
ccccctcagg acggggagag aaccagttcc catactacac cctcccaaag acccgtccct   1320
acatctacca ttcatcccac cacccgcgag acacacattc ctaccactat gaccacatcc   1380
catgacaccg attccaatcg ccctaacccc atcgatatca gcgaatctac cgagcccgga   1440
cccctcacaa atacaacccg cggagccgct aatctgctga ctggctcccg cgcactcga    1500
agagaaatca ccctgcgaac acaggccaag tgtaacccaa acctccatta ttggacaacc   1560
caggatgaag gggccgctat tggcctcgct tggatcccctt atttcgggcc tgcagccgag   1620
gggatctata ccgaaggtat aatgcataat cagaacgggc tgatttgcgg gctgcgccag   1680
ctcgccaacg agactaccca ggccctccag ctctttctcc gggctactac cgaactgcga   1740
accttttcca ttctcaatag gaaagctatc gatttcttgc tccagcgctg ggggggaacc   1800
tgtcatatcc tcggacccga ttgctgtatt gagccacatg attggactaa aaacatcact   1860
gacaaaattg atcagatcat tcatgatttc attgataaac ccctccccga tcagactgat   1920
aatgacaatt ggtggacggg atggcgccag tgggtgcccg ctgggattgg cattacaggt   1980
gtcattattg ccgtgattgc actcctgtgt atctgtaaat ttctgctgtg a             2031
```

<210> SEQ ID NO 12
<211> LENGTH: 2031
<212> TYPE: DNA
<213> ORGANISM: Sudan ebolavirus strain Gulu

<400> SEQUENCE: 12

```
atgggcggcc tgagcctgct gcagctgccc cgggacaagt tccggaagtc cagcttcttc      60
gtgtgggtga tcatcctgtt ccagaaagcc ttcagcatgc ccctgggcgt ggtgaccaac     120
agcaccctgg aagtgaccga gatcgaccag ctggtgtgca aggaccacct ggccagcacc     180
gatcagctga agtccgtggg cctgaacctg gaaggcagcg cgtgagcac cgacatcccc     240
agcgccacca agagatgggg cttcagatcc ggcgtgcccc ccaaggtggt gtcttatgag     300
```

```
gccggcgagt gggccgagaa ctgctacaac ctggaaatca agaagcccga cggcagcgag    360
tgtctgcctc cccctcccga tggcgtgaga ggcttccccc ggtgcagata cgtgcacaag    420
gcacaaggca ccggtccatg cccaggcgac tacgccttcc acaaggacgg cgcctttttc    480
ctgtacgacc ggctggcctc caccgtgatc taccggggcg tgaactttgc cgagggcgtg    540
atcgccttcc tgatcctggc caagcccaaa gagacattcc tgcagagccc cccatccgg     600 gaggccgtga actacaccga aacaccagc agctactacg ccacctccta cctggaatac    660
gagatcgaga acttcggcgc ccagcacagc accaccctgt tcaagatcga caacaacacc    720
ttcgtgcggc tggacagacc ccacaccccc cagtttctgt tccagctgaa cgacaccatc    780
catctgcatc agcagctgtc caacaccacc ggcagactga tctggaccct ggacgccaac    840
atcaacgccg acatcggtga atgggctttt tgggagaaca agaagaatct gagcgagcag    900
ctgcggggcg aagaactcag cttcgaggcc ctgagcctga cgagacaga ggacgacgac    960 gccgccagca gccggatcac caagggccgg atcagcgacc gggccaccag aaagtacagc   1020
gacctggtgc ccaagaacag ccccggcatg gtgcctctgc acatccccga gggcgagaca   1080
actctcccta gtcagaatag caccgagggc agacgcgtgg gcgtgaacac ccaggaaacc   1140
atcaccgaga cagccgccac catcattggt actaacggca accacatgca gatcagcacc   1200
atcggcatcc ggcccagcag cagccagatc ccaagtagta gtcctaccac agcccctagc   1260
cctgaggccc agacccctac cacacacacc agcggcccta gcgtgatggc caccgaggaa   1320
cctaccaccc ctcctggcag cagcccaggt ccaactaccg aggcaccaac cctgaccacc   1380
cccgagaaca tcaccaccgc cgtgaaaacc gtgctgcccc aggaaagcac cagcaacggc   1440
ctgatcacca gcaccgtgac cggcatcctg gcagcctgg gcctgcggaa gcggagcaga   1500
cggcagacca acaccaaggc caccggcaag tgcaacccca acctgcacta ctggaccgcc   1560
caggaacagc acaacgccgc tgggatcgcc tggatcccct actttggtcc tgtgctgag    1620 ggaatataca ccgagggcct gatgcacaac cagaacgccc tggtgtgcgg cctgagacag   1680
ctggccaacg aaaccactca ggcactgcag ctgttcctgc gggccaccac cgagctgcgg   1740
acctacacca tcctgaacag gaaggccatc gactttctgc tgcggagatg gggcggcacc   1800
tgtagaatcc tgggccccga ctgctgcatc gagccccacg actggaccaa gaatatcacc   1860
gacaagatca accagatcat ccacgacttc atcgacaacc ccctgcccaa ccaggacaac   1920
gacgacaact ggtggactgg ttggcgacag tggatccctg ccggcatcgg catcaccggc   1980
atcatcattg ccattatcgc tctcctctgc gtgtgcaagc cctctgctg a             2031
```

<210> SEQ ID NO 13
<211> LENGTH: 2031
<212> TYPE: DNA
<213> ORGANISM: Zaire ebolavirus Mayinga strain

<400> SEQUENCE: 13

```
atgggcgtga caggcattct gcagctcccc agagacagat tcaagcggac ctccttttc      60 ctctgggtca tcattctgtt tcagcggacc ttctccatcc ctctgggcgt gatccacaat    120
agcaccctcc aggtgtccga cgtggacaag ctcgtgtgcc gggacaagct gtcctccacc    180
aaccagctga gaagcgtggg gctgaatctc gagggcaatg gcgtggccac agacgtgccc    240
tccgccacaa agcgctgggg cttccggagc ggcgtccctc ctaaagtcgt gaactacgag    300
gcaggggaat gggctgaaaa ttgttacaat ctcgagatca aaaaaccaga tggctctgag    360
```

```
tgcctgcctg ccgcaccaga cggcatcagg ggcttcccta gatgccgcta tgtgcacaag    420
gtgagtggta caggcccttg tgccggcgat tttgcctttc acaaagaggg ggctttcttt    480
ctgtacgaca ggctcgccag tacagtgata taccgaggta ctaccttcgc cgaaggcgtg    540
gtggcctttc tgattctgcc ccaggccaag aaggacttct tcagcagcca cccctgaga    600 gaacccgtga acgccacaga ggacccagc agcggctact acagcaccac aatcagatac    660
caggccacag gcttcggcac caatgagaca gagtacctgt tcgaggtgga caacctgacc    720
tacgtgcagc tggaaagccg gtttacccct cagttcctcc tgcagctcaa cgagacaatc    780
tacacctccg gcaagcggag caacacaaca ggcaagctca tctggaaagt gaaccccgag    840
atcgatacca ctataggga gtgggctttc tgggaaacta agaagaacct cacccggaag    900
atcagatccg aggaactgtc cttcaccgtg gtgtccaacg gcgccaagaa catttcagga    960
cagagccccg ccagaacaag cagcgacccc ggcaccaaca ccacaaccga ggaccacaag    1020
atcatggcca gcgagaactc cagcgccatg gtgcaggtcc acagccaggg aagagaagcc    1080
gccgtgagcc acctgaccac actggccacc atcagcacca gccccagag cctgaccacc    1140 aagcctggcc ccgacaacag cacacacaac accccgtgt acaagctgga catcagcgag    1200
gccacccagg tggagcagca ccacagacgg accgacaacg acagcaccgc cagcgatacc    1260
ccttctgcca ccacagccgc cggaccccct aaggccgaga ataccaacac cagcaagagc    1320
accgactttc tggatccagc caccaccacc agtccacaga accacagcga aaccgccggc    1380
aacaacaata cccaccacca ggacaccggc gaggaaagcg ccagctctgg caagctgggc    1440
ctgattacca acacaatcgc cggcgtggcc ggactgatca ccggcggcag acggaccaga    1500
cgggaggcca tcgtgaacgc ccagcccaaa tgtaatccta atctccacta ttggaccaca    1560
caggacgagg cgctgccat cggactggca tggattcctt acttcggacc agccgctgaa    1620
gggatctata tcgagggct catgcataac caggatggtc tgatttgtgg tctccggcag    1680
ctggctaatg agacaacaca ggctctccag ctgtttctga gagccacaac agagctgaga    1740
accttcagca ttctcaaccg caaggctatt gacttcctgc tccaacgatg gggaggcaca    1800
tgccacatcc tggggcctga ttgttgtatc gaacctcacg attggacaaa gaacattaca    1860
gataagatcg atcagattat ccatgacttt gtggacaaga ccctgcccga tcagggcgac    1920
aacgataatt ggtggacagg gtggagacag tggattccag ccgggattgg cgtgaccggc    1980
gtgattatcg ccgtgatcgc cctgttctgc atctgcaagt tcgtgttctg a            2031
```